United States Patent
Kleuskens et al.

(10) Patent No.: US 10,159,611 B2
(45) Date of Patent: *Dec. 25, 2018

(54) FIXED AND REMOVABLE ABSORBENT CORES FOR ABSORBENT ARTICLES

(71) Applicant: KIMBERLY-CLARK WORLDWIDE, INC., Neenah, WI (US)

(72) Inventors: Sarah Austin Kleuskens, Neenah, WI (US); Marcille F. Ruman, Oshkosh, WI (US); Stephen D. Franger, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/515,463

(22) PCT Filed: Sep. 24, 2015

(86) PCT No.: PCT/US2015/051819
§ 371 (c)(1),
(2) Date: Mar. 29, 2017

(87) PCT Pub. No.: WO2016/053724
PCT Pub. Date: Apr. 7, 2016

(65) Prior Publication Data
US 2017/0216111 A1 Aug. 3, 2017

Related U.S. Application Data

(60) Provisional application No. 62/057,026, filed on Sep. 29, 2014.

(51) Int. Cl.
*A61F 13/505* (2006.01)
*A61F 13/515* (2006.01)
(Continued)

(52) U.S. Cl.
CPC ............ *A61F 13/665* (2013.01); *A61F 13/15* (2013.01); *A61F 13/49* (2013.01); *A61F 13/496* (2013.01);
(Continued)

(58) Field of Classification Search
CPC .. A61F 13/474; A61F 13/4906; A61F 13/493; A61F 13/505; A61F 13/515;
(Continued)

(56) References Cited

U.S. PATENT DOCUMENTS 3,842,838 A 10/1974 Gellert
4,019,517 A * 4/1977 Glassman ............. A61F 13/493
604/359
(Continued)

FOREIGN PATENT DOCUMENTS

CN 1205624 A 1/1999
EP 0 830 122 B1 11/2000
(Continued)

OTHER PUBLICATIONS

Co-pending U.S. Appl. No. 15/515,440, filed Mar. 29, 2017, by Kleuskens et al. for "Fixed and Removable Absorbent Cores for Absorbent Articles."
(Continued)

*Primary Examiner* — Lynne Anderson
(74) *Attorney, Agent, or Firm* — Kimberly-Clark Worldwide, Inc.

(57) ABSTRACT

A multiple use absorbent article includes a chassis absorbent unit having a chassis topsheet, a chassis backsheet, and a chassis absorbent core sandwiched between the chassis topsheet and the chassis backsheet. The article also includes an absorbent insert bonded to the chassis absorbent unit, a removable portion of the absorbent insert configured to be selectively removable from the chassis absorbent unit,
(Continued)

wherein the absorbent insert includes an insert topsheet, an insert backsheet, and an insert absorbent core sandwiched between the insert topsheet and the insert backsheet. The absorbent insert further includes a line of weakness that provides for separation of the absorbent insert into a removable portion configured to be removed from the chassis absorbent unit, and a resident portion that remains bonded to the chassis absorbent unit.

15 Claims, 19 Drawing Sheets

(51) Int. Cl.
| | |
|---|---|
| *A61F 13/66* | (2006.01) |
| *A61F 13/15* | (2006.01) |
| *A61F 13/496* | (2006.01) |
| *A61F 13/53* | (2006.01) |
| *A61F 13/539* | (2006.01) |
| *A61F 13/56* | (2006.01) |
| *A61F 13/49* | (2006.01) |

(52) U.S. Cl.
CPC ............ *A61F 13/505* (2013.01); *A61F 13/53* (2013.01); *A61F 13/539* (2013.01); *A61F 13/56* (2013.01); *A61F 13/5616* (2013.01); *A61F 13/515* (2013.01); *A61F 2013/16* (2013.01); *A61F 2013/49066* (2013.01); *A61F 2013/49087* (2013.01); *A61F 2013/49088* (2013.01); *A61F 2013/53908* (2013.01); *A61F 2013/53991* (2013.01)

(58) Field of Classification Search
CPC .. A61F 13/539; A61F 13/665; A61F 2013/16; A61F 2013/49063; A61F 2013/49066; A61F 2013/49087; A61F 2013/5055; A61F 2013/53908; A61F 2013/53916; A61F 2013/53925; A61F 2013/53933; A61F 2013/53941; A61F 2013/5395; A61F 2013/53958; A61F 2013/53966; A61F 2013/53991
See application file for complete search history.

(56) References Cited

U.S. PATENT DOCUMENTS

| | | | |
|---|---|---|---|
| D269,907 S | 7/1983 | Tong | |
| 4,842,596 A | 6/1989 | Kielpikowski et al. | |
| D309,020 S | 7/1990 | Jannoni et al. | |
| 4,938,756 A | 7/1990 | Salek | |
| 4,964,857 A | 10/1990 | Osborn | |
| 5,217,447 A | 6/1993 | Gagnon | |
| 5,405,342 A | 4/1995 | Roessler et al. | |
| 5,458,591 A | 10/1995 | Roessler et al. | |
| 5,460,624 A | 10/1995 | Ahr et al. | |
| 5,820,616 A | 10/1998 | Homey | |
| H1788 H | 2/1999 | Christon et al. | |
| 5,910,137 A * | 6/1999 | Clark | A61F 13/505 604/385.04 |
| 6,013,064 A | 1/2000 | Yamada | |
| 6,280,427 B1 * | 8/2001 | Maggiulli | A61F 13/474 604/385.01 |
| 6,468,257 B1 | 10/2002 | Ono et al. | |
| D470,935 S | 2/2003 | Sherrod et al. | |
| 6,605,071 B1 | 8/2003 | Gray et al. | |
| 6,623,466 B1 | 9/2003 | Richardson | |
| 6,793,649 B1 | 9/2004 | Fujioka et al. | |
| 6,840,926 B2 * | 1/2005 | Nukina | A61F 13/474 604/385.01 |
| 6,921,393 B2 | 7/2005 | Tears et al. | |
| 7,175,613 B2 | 2/2007 | Sugiyama et al. | |
| 7,264,615 B2 | 9/2007 | Sherrod et al. | |
| 7,387,620 B2 | 6/2008 | Watanabe et al. | |
| D621,501 S | 8/2010 | Coon | |
| 7,766,887 B2 | 8/2010 | Burns, Jr. et al. | |
| 7,842,020 B2 * | 11/2010 | Hurwitz | A61F 13/493 604/368 |
| 7,938,814 B2 * | 5/2011 | Koyama | A61F 13/15203 604/378 |
| D647,200 S | 10/2011 | Slaughter | |
| 8,585,667 B2 | 11/2013 | Roe et al. | |
| 8,652,115 B2 | 2/2014 | Roe et al. | |
| 8,702,673 B1 | 4/2014 | Jones | |
| 2003/0088224 A1 | 5/2003 | Ceman et al. | |
| 2005/0049569 A1 | 3/2005 | Tracy | |
| 2008/0119812 A1 | 5/2008 | Hurwitz | |
| 2009/0112174 A1 | 4/2009 | Drevik et al. | |
| 2010/0318057 A1 | 12/2010 | Yakem | |
| 2012/0022485 A1 | 1/2012 | Roe et al. | |
| 2013/0338620 A1 | 12/2013 | Speak | |
| 2014/0005621 A1 | 1/2014 | Roe et al. | |

FOREIGN PATENT DOCUMENTS

| | | |
|---|---|---|
| EP | 0 767 644 B1 | 11/2001 |
| EP | 1 097 683 B1 | 1/2005 |
| GB | 2 440 314 A | 1/2008 |
| JP | 3058259 U | 6/1999 |
| WO | WO 1991/016871 A1 | 11/1991 |
| WO | WO 1998/017220 A1 | 4/1998 |
| WO | WO 2006/108029 A1 | 10/2006 |
| WO | WO 2013/135711 A1 | 9/2013 |
| WO | WO 2015/094029 A1 | 6/2015 |

OTHER PUBLICATIONS

Co-pending U.S. Appl. No. 15/515,456, filed Mar. 29, 2017, by Kleuskens et al. for "Fixed and Removable Absorbent Cores for Absorbent Articles."

* cited by examiner

FIXED AND REMOVABLE ABSORBENT CORES FOR ABSORBENT ARTICLES

BACKGROUND

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

Changing such absorbent articles can be difficult, especially when away from home. For example, to change step-in incontinence pants on the go, the user must remove their pants and shoes before donning a fresh or replacement product. The previous product can be removed by tearing the side seams and without removing clothing, but a second clean product cannot be applied without removing clothing.

While it is also known to include multiple absorbent articles stacked in a compound configuration, such that a series of absorbent articles are adhesively attached one atop the other, so as to allow the user to remove one article at a time, such configuration often leads to relatively bulky products and side leakage problems.

SUMMARY

The present disclosure provides an opportunity to improve the changing experience while making it easy and intuitive to use. A new absorbent article system is required to solve these problems. The elements of the absorbent article system are generally a primary absorbent article with a secondary absorbent insert.

The present disclosure overcomes the problems by providing a multiple use absorbent article including a chassis absorbent unit having a chassis topsheet, a chassis backsheet, and a chassis absorbent core sandwiched between the chassis topsheet and the chassis backsheet. The article also includes an absorbent insert bonded to the chassis absorbent unit, a removable portion of the absorbent insert configured to be selectively removable from the chassis absorbent unit, wherein the absorbent insert includes an insert topsheet, an insert backsheet, and an insert absorbent core sandwiched between the insert topsheet and the insert backsheet. The absorbent insert further includes a line of weakness that provides for separation of the absorbent insert into a removable portion configured to be removed from the chassis absorbent unit, and a resident portion that remains bonded to the chassis absorbent unit.

The present disclosure also provides a multiple use absorbent article including a chassis absorbent unit having a liquid permeable chassis topsheet, a liquid impermeable chassis backsheet, and a chassis absorbent core sandwiched between the chassis topsheet and the chassis backsheet. The article also includes an absorbent insert bonded to the chassis absorbent unit, a removable portion of the absorbent insert configured to be selectively removable from the chassis absorbent unit, wherein the absorbent insert comprises an insert topsheet, an insert backsheet, and an insert absorbent core sandwiched between the insert topsheet and the insert backsheet. The insert absorbent core is sealed by a peripheral sealing region between the insert topsheet and the insert backsheet adjacent at least a peripheral edge of the insert topsheet and the insert backsheet. The absorbent insert further includes a line of weakness disposed within the peripheral sealing region that provides for separation of the absorbent insert into a removable portion configured to be removed from the chassis absorbent unit, and a resident portion that remains bonded to the chassis absorbent unit.

The present disclosure provides several attributes that are advantageous. An absorbent article system with a removable absorbent insert enhances the efficiency of the absorbent-article-using process, helps to better care for the user, and can be more cost effective. Benefits of such a system to a business include a reduction of absorbent article machine capital expenditure, optimized manufacturing, and more rapid evaluation and introduction of product improvements.

Other objects and advantages of the present disclosure will become more apparent to those skilled in the art in view of the following description and the accompanying drawings.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
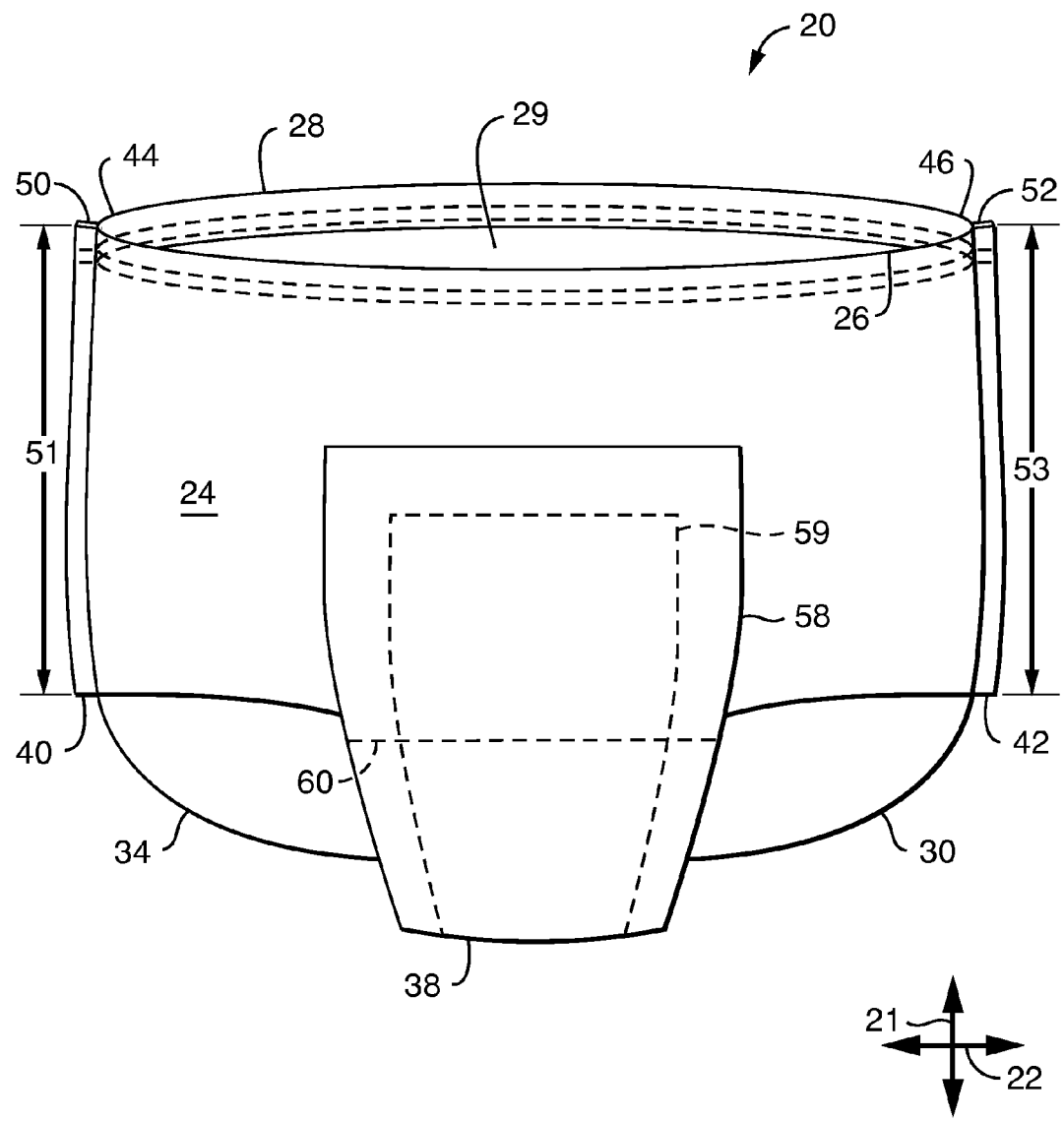
FIG. 1 representatively illustrates a front perspective view of a disposable absorbent article incorporating principles of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects of the present disclosure only, and is not intended as limiting the broader aspects of the present disclosure.

In general, the present disclosure is directed to an absorbent article containing at least one removable absorbent and at least one non-removable absorbent as part of the base article chassis. The absorbent insert includes a liquid permeable, user-facing liner or topsheet, an absorbent core, and a garment-facing backsheet or outer cover. The absorbent core is sandwiched between, and can be bonded between, the topsheet and the backsheet. At least the backsheet of the absorbent insert is attached to the chassis with bonding around the perimeter of the absorbent insert and includes a line of weakness or perforation inside the bonded perimeter such that a portion of the absorbent insert can be easily removed, leaving a portion of the absorbent insert behind and attached to the chassis. The bonded perimeter of the absorbent insert is lateral to the line of weakness along peripheral edges of the absorbent insert, such that the bonding does not preferably extend in the depth direction of the article, in the line of weakness region. The base chassis also has at least a liner or topsheet, absorbent core, and a liquid impervious backsheet or outer cover similar to the absorbent insert. Removable portions of an absorbent insert can have a removal feature that can be a pull tab, notch, or other means to facilitate removal of the removable portion of the absorbent insert from the non-removable, resident portion of the absorbent insert. In other aspects, the absorbent insert and the non-removable absorbent can have side barriers (e.g., flaps) to protect the remaining absorbent article materials from being soiled and to prevent urine/BM leakage.

One aspect of the disclosure described herein can be seen as a system of a primary absorbent article with a secondary absorbent insert. For purposes of illustration, and not for purposes of limitation, the absorbent article system is described as it would apply to a particular design of an incontinence pant. The same system, however, can be described using another design, another suitable absorbent article, undergarment, pad, garment, or other wearable article.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Disposable" refers to articles that are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite that can be elongated by at least percent of its relaxed length and that will recover, upon release of the applied force, at least 20 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Layer" when used in the singular can have the dual meaning of a single element or a plurality of elements.

"Longitudinal" and "transverse" have their customary meaning, as indicated by the longitudinal and transverse axes depicted in the figures. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction when the article is in a fully stretched and laid-flat condition, prior to the joining of the side seams.

"Member" when used in the singular can have the dual meaning of a single element or a plurality of elements.

The term "body side" should not be interpreted to mean in contact with the body of the user, but rather simply means the side that would face toward the body of the user when the article is applied to the user, regardless of whether the absorbent article is actually being worn by the user and regardless of whether there are or can be intervening layers between the component and the body of the user. Likewise, the term "garment side" should not be interpreted to mean in contact with the garments of the user, but rather simply means the side that faces away from the body of the user when the garment is applied to the user, and therefore toward any outer garments that can be worn by the user, regardless of whether the absorbent article is actually being worn by a user, regardless of whether any such outer garments are actually worn and regardless of whether there can be intervening layers between the component and any outer garment.

The term "disposable absorbent article" as used herein is an article that is intended to be worn by persons, including infants, toddlers or adults, which is designed for a single or temporary use and is meant to be disposed of after being used once instead of being laundered or dry cleaned for re-use.

The term "line of weakness" refers to any region or area of weakened material, preferably having a length and that might or might not have a defined width, and can include linear and non-linear patterns, such as curvilinear patterns of weakness, or other shapes, such as circles, rectangles, etc. The line of weakness can include a perforation or other series of cuts, a thinning, or breakage or separation of material, or a strip of a different kind of material bridging between adjacent portions of material, that is more easily torn or broken than the adjacent portions, and that allow the user or manufacturer to separate the adjacent portions along the line of weakness.

The term "bonded area" refers to the region of the chassis topsheet and/or the chassis backsheet that is bonded to the absorbent insert. The resident portion of the absorbent insert that remains attached to the chassis absorbent unit following removal of the removable portion of the absorbent insert is largely coincident with the bonded area; the area of the absorbent insert that is bonded to the chassis absorbent unit defines the bonded area.

Reference to FIGS. 1-20 shall be made in describing various aspects of the disclosure. It should be noted that the aspects depicted in FIGS. 1-20 are merely representative examples of the article and process of the disclosure. Although for illustrative purposes certain features of the present disclosure shall be described and illustrated with respect to an adult incontinence article, the various aspects of the present disclosure are equally suitable for use with disposable diapers, disposable swim pants, disposable training pants, disposable enuresis garments, disposable menstrual products, and the like.

Figure 2:
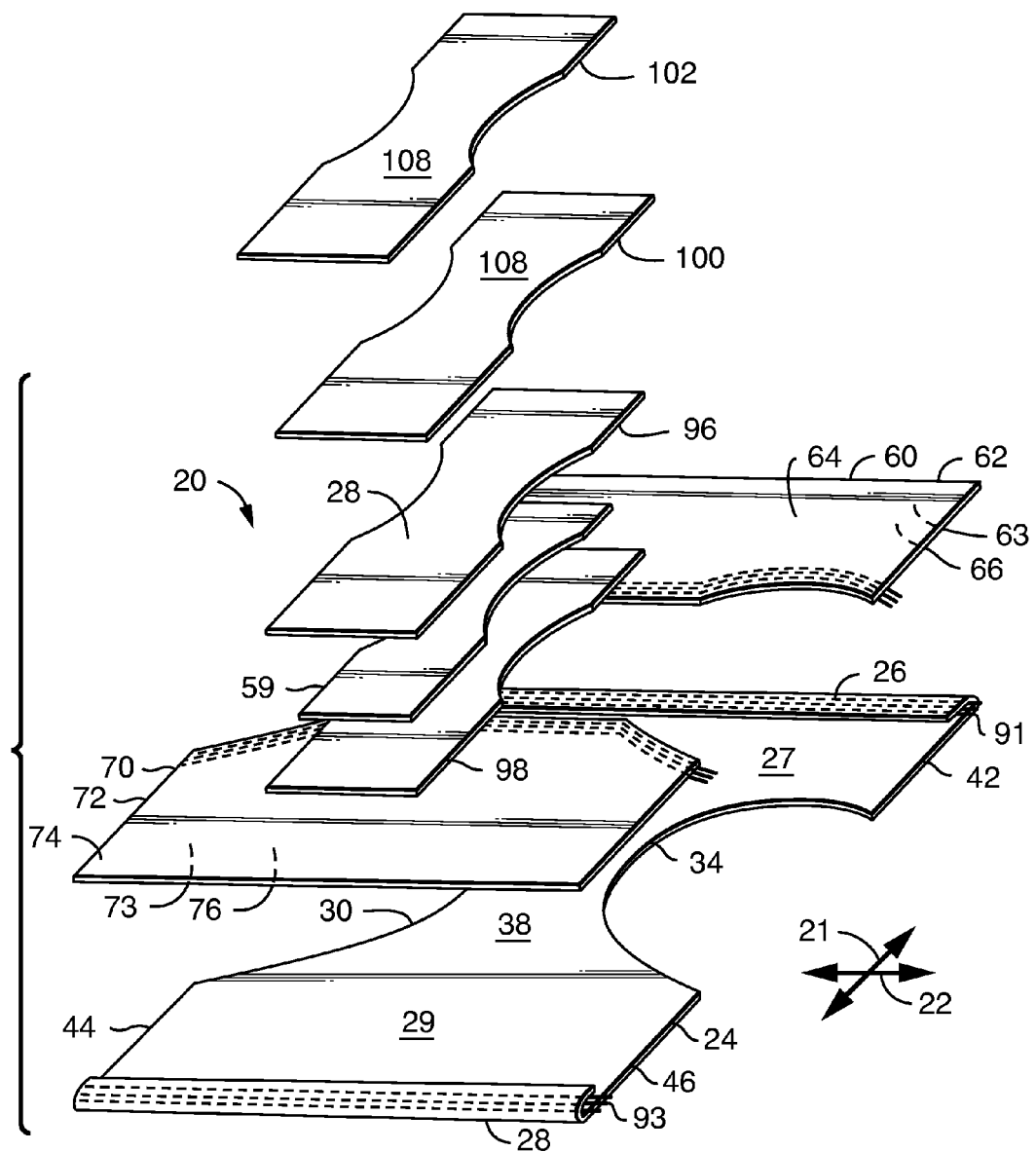
FIG. 2 representatively illustrates an exploded perspective view of the article of FIG. 1.

Referring to FIGS. 1 and 2, a particular aspect of a disposable absorbent article 20 of the present disclosure defines a longitudinal direction 21 and a transverse direction 22, and includes an outer cover 24. The outer cover 24 defines a front end edge 26, a back end edge 28 longitudinally opposite the front end edge 26, and first and second transversely opposed leg edges 30 and 34 positioned longitudinally between the front end edge 26 and the back end edge 28. The outer cover 24 defines a front region 27 adjacent the front end edge 26, a back region 29 adjacent the back end edge 28, and a crotch region 38 positioned longitudinally between the front region 27 and back region 29.

The outer cover 24 further defines first and second transversely opposed front side edges 40 and 42. The outer cover 24 also defines first and second transversely opposed back side edges 44 and 46. While it is contemplated that an article may be refastenable, the illustrated article (see FIG. 1) includes a first side seam 50 at which the first front side edge 40 is attached to the first back side edge 44 and that defines a first side seam length 51. The article further includes a second side seam 52 at which the second front side edge 42 is attached to the second back side edge 46 and that defines a second side seam length 53.

The article 20 optionally includes an elastomeric front body panel 60 superposed on and attached to the front region 27 of the outer cover 24. It is contemplated, although not illustrated, that the article can be non-elastic or at least partially non-elastic, such that optional elastic components can be included at only the waist and/or leg regions. In the illustrated aspect, the front body panel 60 comprises an elastomeric film laminate 62 that extends transversely from the first front side edge 40 to the second front side edge 42. The article also includes an elastomeric back body panel 70 superposed on and attached to the back region 29 of the outer cover 24. As with the front body panel 60 described above, the back body panel 70 comprises an elastomeric film laminate 72 that extends transversely from the first back side edge 44 to the second back side edge 46.

The article 20, which includes the main chassis of the article 20, also includes a chassis absorbent unit 58 superposed over the crotch region 38 of the outer cover 24. The chassis absorbent unit 58 includes a chassis absorbent core 59, and in particular aspects includes a chassis topsheet 96 and a chassis backsheet 98. In other products a topsheet can be called a liner, a body-facing surface, or other equivalent. In other products a backsheet can be called an outer cover, a garment-facing surface, or other equivalent. U.S. Patent Application Publications US 2008/0095978 and US 2009/0197041, both assigned to Kimberly-Clark Worldwide, Inc., provide examples of technology suitable for use in creating the front and back body panel elastomeric film laminates, although other elastomeric film laminates can also be used. The chassis absorbent core 59 can be any suitable size or shape depending in part on the kind, shape, and size of the absorbent article 20.

In certain aspects and as representatively illustrated in FIG. 2, the front body panel 60 is longitudinally spaced from and distinct from the back body panel 70. In particular aspects, as representatively illustrated in FIGS. 1 and 2, at least a portion of the chassis absorbent unit 58 is superposed over a portion of the front body panel 60. Similarly, in particular aspects and as representatively illustrated in FIG. 2, at least a portion of the chassis absorbent unit 58 is superposed over a portion of the back body panel 70. In such aspects, it can optionally be the case that a majority of the area of the portion of the front body panel (and/or of the back body panel) superposed by the at least a portion of the chassis absorbent unit 58 includes a substantially deadened/inactivated elastomeric film.

In particular aspects, the elastomeric film laminate 62 in the front body panel 60 includes a front body panel elastomeric film side or layer 63 and a front body panel nonwoven side or layer 64. Preferably, in such an aspect, a bodyside surface 65 of the elastomeric film side or layer 63 is directly adhered to the nonwoven layer 64, and a garment-side surface 66 of the elastomeric film side or layer 63 is directly adhered to the outer cover 24, as representatively illustrated in FIG. 2. In other aspects (not shown), a garment-side surface 66 of the elastomeric film side or layer 63 is directly adhered to the nonwoven layer 64, and a bodyside surface 65 of the elastomeric film side or layer 63 is directly adhered to the outer cover 24. Similarly, in particular aspects, the elastomeric film laminate 72 in the back body panel 70 comprises a back body panel elastomeric film side or layer 73 and a back body panel nonwoven side or layer 74. Preferably, in such an aspect, a bodyside surface 75 of the elastomeric film side layer 73 is directly adhered to the nonwoven layer 74, and a garment-side surface 76 of the elastomeric film side or layer 73 is directly adhered to the outer cover 24, as representatively illustrated in FIG. 2. In another aspect (not shown), a garment-side surface 76 of the elastomeric film side layer 73 is directly adhered to the nonwoven layer 74, and a bodyside surface 75 of the elastomeric film side or layer 73 is directly adhered to the outer cover 24.

In particular aspects, the article 20 can also include a first back leg elastic member attached to the outer cover 24 adjacent at least a portion of the first leg edge 30, and a second back leg elastic member attached to the outer cover 24 adjacent at least a portion of the second leg edge 34. In particular aspects, the article 20 can also include a first front leg elastic member attached to the outer cover 24 adjacent at least a portion of the first leg edge 30, and a second front leg elastic member attached to the outer cover 24 adjacent at least a portion of the second leg edge 34. Each leg elastic member can include a single strand, ribbon, or strip of elastomeric material, or each can include two or more strands, ribbons, or strips, such as, for example, three strands. The article 20 can further include a front waist elastic member 91 and a back waist elastic member 93.

The absorbent insert 100 described above and illustrated in FIGS. 3-17 is used in conjunction with a disposable absorbent article or other garment, undergarment, pad, or wearable article. Although the absorbent insert 100 is generally shown to extend from the front region 27 through the crotch region 38 and into the back region 29, in various other aspects the absorbent insert 100 can be disposed in only one or two of these regions, and can be any shape and size to suit the intended purpose of the absorbent article 20.

Figure 3:
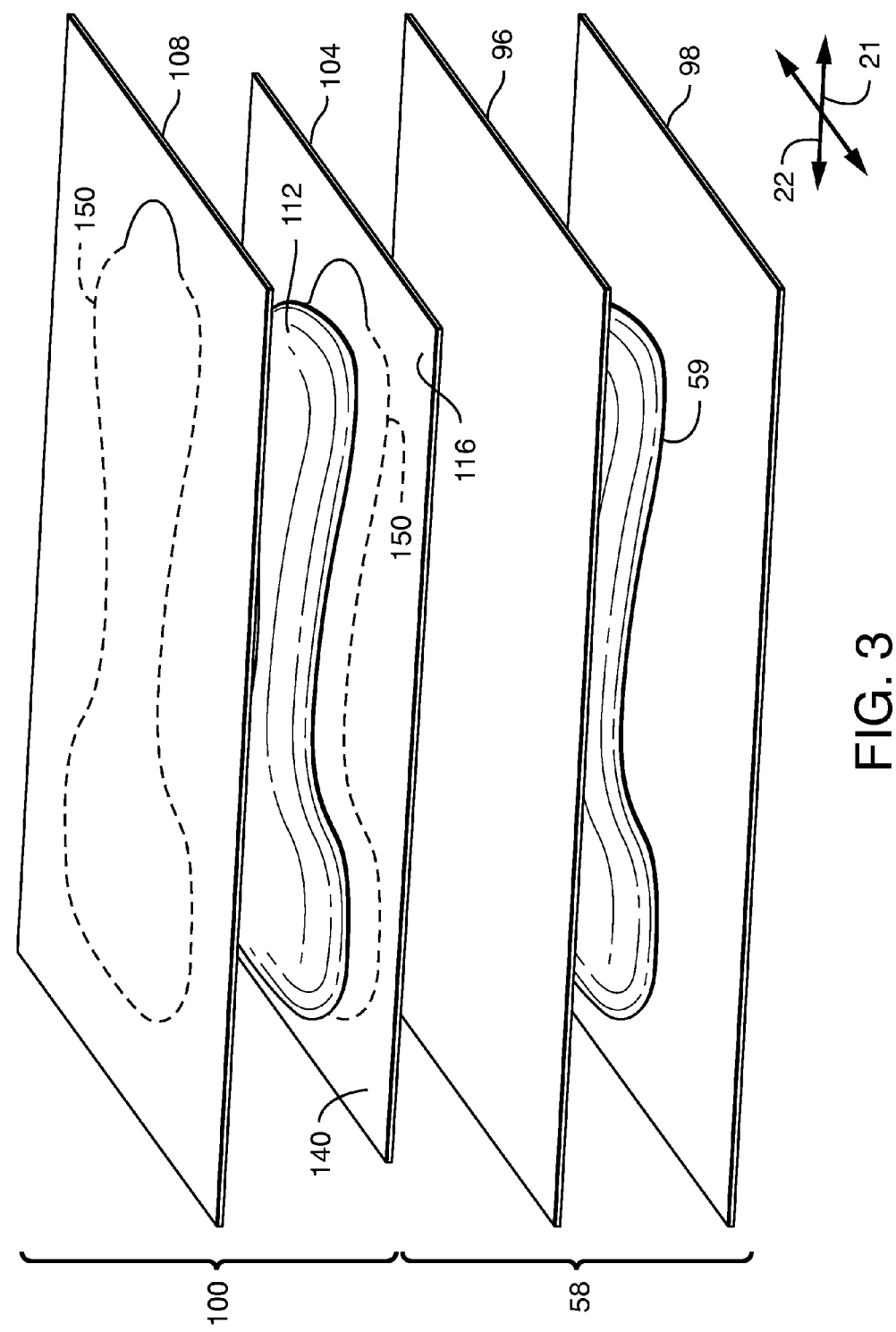
FIG. 3 representatively illustrates an exploded schematic view of the chassis absorbent unit and the absorbent insert of the present disclosure.
Figure 4:
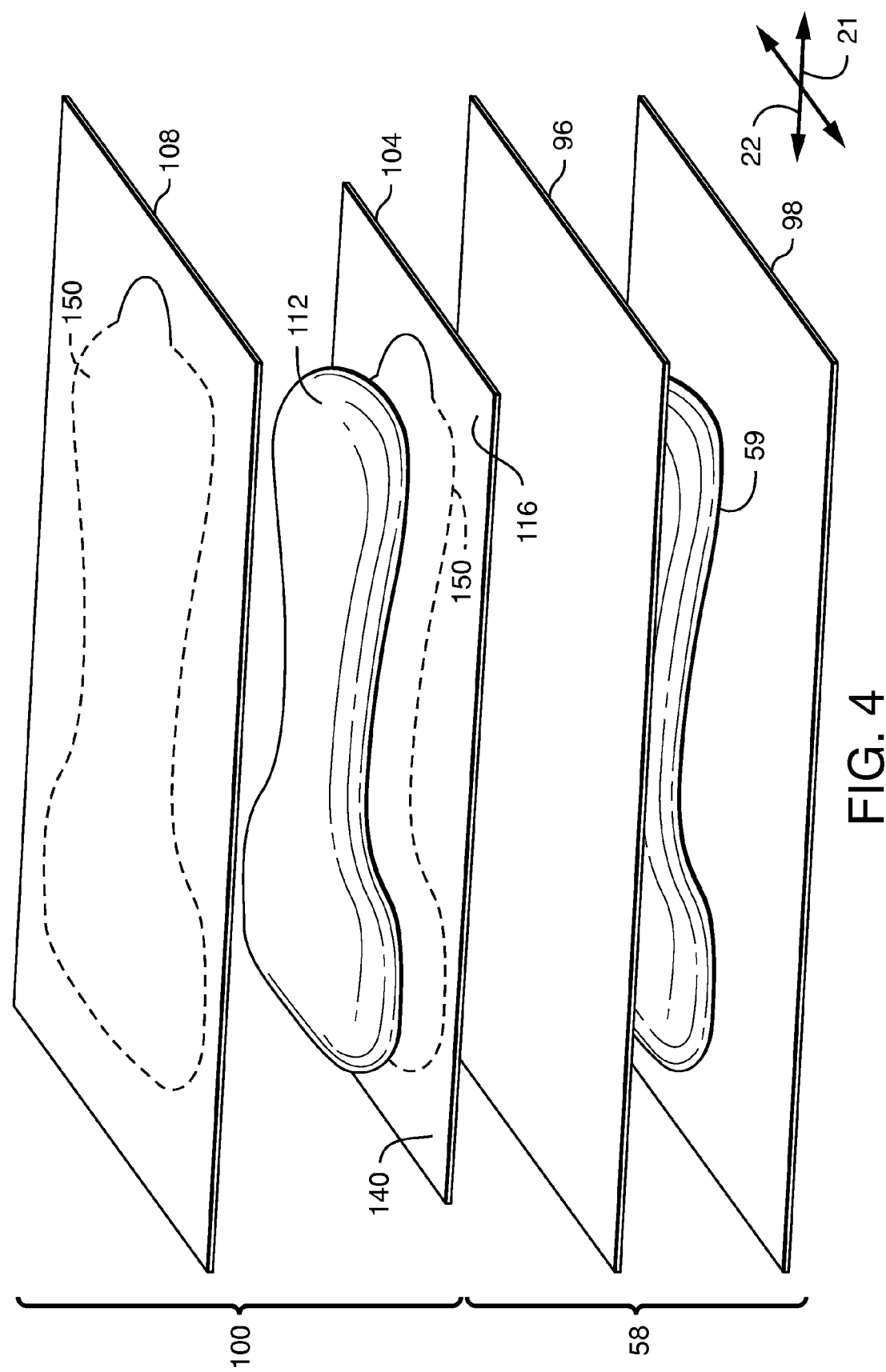
FIG. 4 representatively illustrates an exploded schematic view of the chassis absorbent unit and the absorbent insert of the present disclosure.
Figure 5:
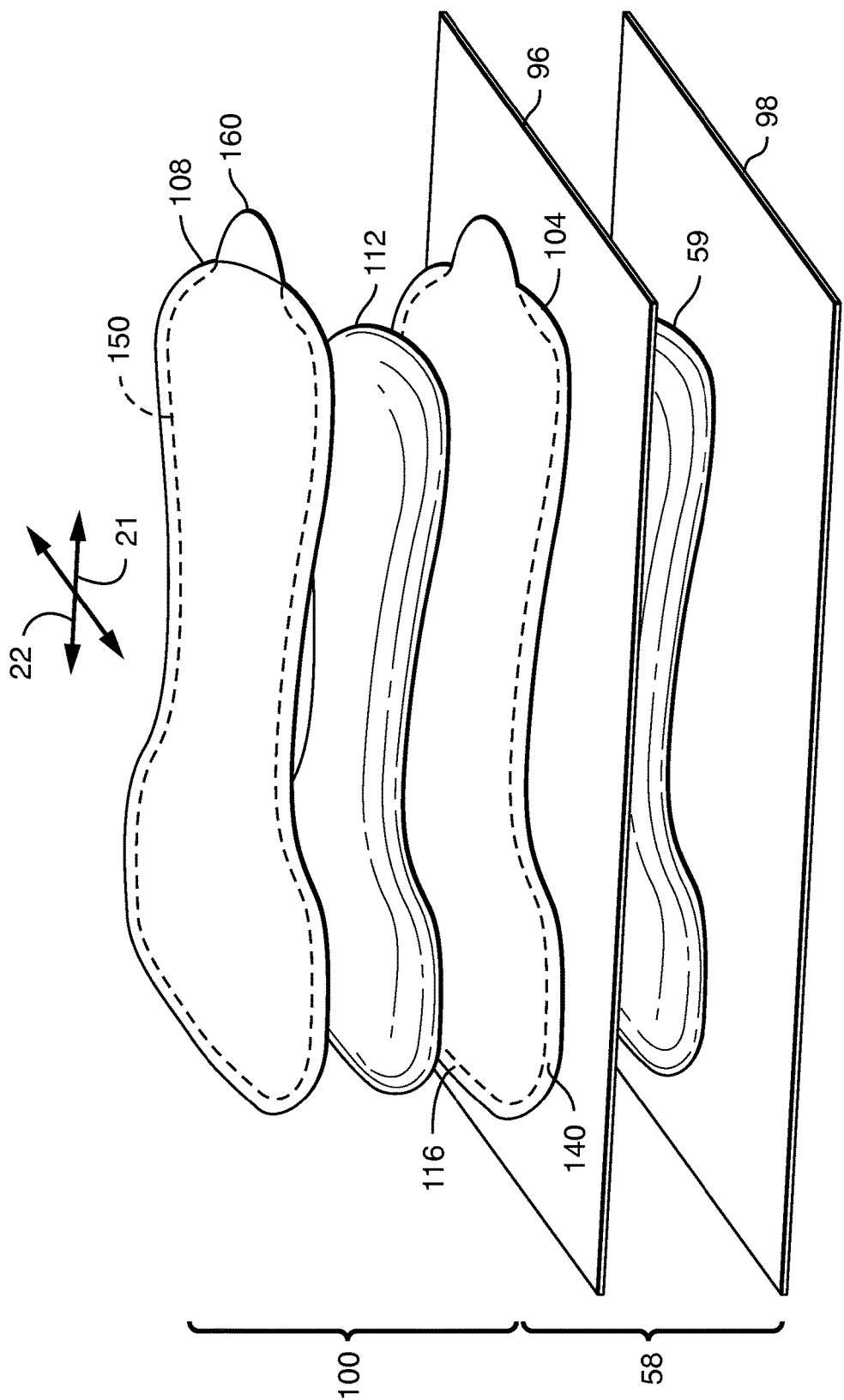
FIG. 5 representatively illustrates an exploded schematic view of the chassis absorbent unit and the absorbent insert of the present disclosure.

As illustrated in FIG. 3, the absorbent insert 100 includes an insert backsheet 104 having a body-facing side and an article-facing side. The absorbent insert 100 can also include an insert topsheet 108 having a body-facing side and an article-facing side. It should be noted that any topsheet in any aspect of the present disclosure can include pleats or other suitable structures (not shown) to accommodate expansion of an absorbent or for other reasons including fit.

The insert topsheet 108 generally includes a liquid-permeable nonwoven to allow bodily fluid to pass through the insert topsheet 108. The insert backsheet 104 can be either liquid-permeable, liquid impermeable, or somewhere in between depending on how much bodily fluid is intended to pass therethrough. For example, for an absorbent insert 100 designed to be used in conjunction with a disposable absorbent article 20 as described herein, the insert backsheet 104 would typically be liquid impermeable to prevent or at least slow bodily fluid from contacting the chassis absorbent unit 58. The insert backsheet 104 and the insert topsheet 108 can be manufactured from the same materials as described above for the chassis backsheet 98 and the chassis topsheet 96.

The absorbent insert 100 can include an insert absorbent core 112 disposed between the insert backsheet 104 and insert topsheet 108. In one aspect, the insert absorbent core 112 includes the same materials described above with respect to the chassis absorbent core 59. The insert absorbent core 112 and the chassis absorbent core 59 can have the same or different absorbencies, and can be comparable to typical products, added capacity products, or any other suitable absorbencies. As with the chassis absorbent core 59, the insert absorbent core 112 can be any suitable size or shape depending in part on the kind, shape, and size of the absorbent article 20. Product flexibility considerations influence the choice of absorbencies and absorbent materials. In various aspects, the absorbent can be greater than 50 percent superabsorbent material. Surge material can also be included in either or both of the chassis absorbent core 59 and the insert absorbent core 112. The chassis absorbent core 59 and/or the insert absorbent core 112 can be shaped or rectangular and can include other layers or materials suitable for use in an absorbent core. In addition, absorbent material and/or other materials such as tissue can be reduced or removed in the crotch region 38 of the chassis absorbent core 59 and/or the portion of the insert absorbent core 112 adjacent the crotch region 38 both to enhance the fit properties of the absorbent article 20 and to enhance the sealing properties in that region. For example, ultrasonic bonding works best when a polymer is bonded to a polymer or a nonwoven is bonded to a nonwoven without intervening materials such as tissue. Reducing or removing absorbent material and/or other materials such as tissue in the crotch region 38 of the chassis absorbent core 59 and/or the portion of the insert absorbent core 112 adjacent the crotch region 38 makes for better bonding, and enhances sealing properties to better contain absorbent materials.

When used in conjunction with a disposable absorbent article 20, the absorbent insert 100 can be positioned on the inner surface 28 of the chassis topsheet 96.

In certain aspects, topsheet material is used to cover both the chassis absorbent core 59 and the absorbent insert 100. In one aspect illustrated in FIG. 3, the chassis and insert topsheets 96, 108 can both be full length and width with respect to the chassis backsheet 98. This, however, can be a more expensive execution and could add stiffness to the product. In another aspect illustrated in FIG. 4, the chassis topsheet 96 can be full length and the insert topsheet 112 can be full length but narrower. The narrower part could be shaped to match leg cutout and/or crotch elastics. In still another aspect illustrated in FIG. 5, the chassis topsheet 96 can be full length and the insert topsheet 112 can be shorter and narrower in a cut and place execution. The insert topsheet 112 can be shaped to match the contour of the insert absorbent core shape.

Figure 6:
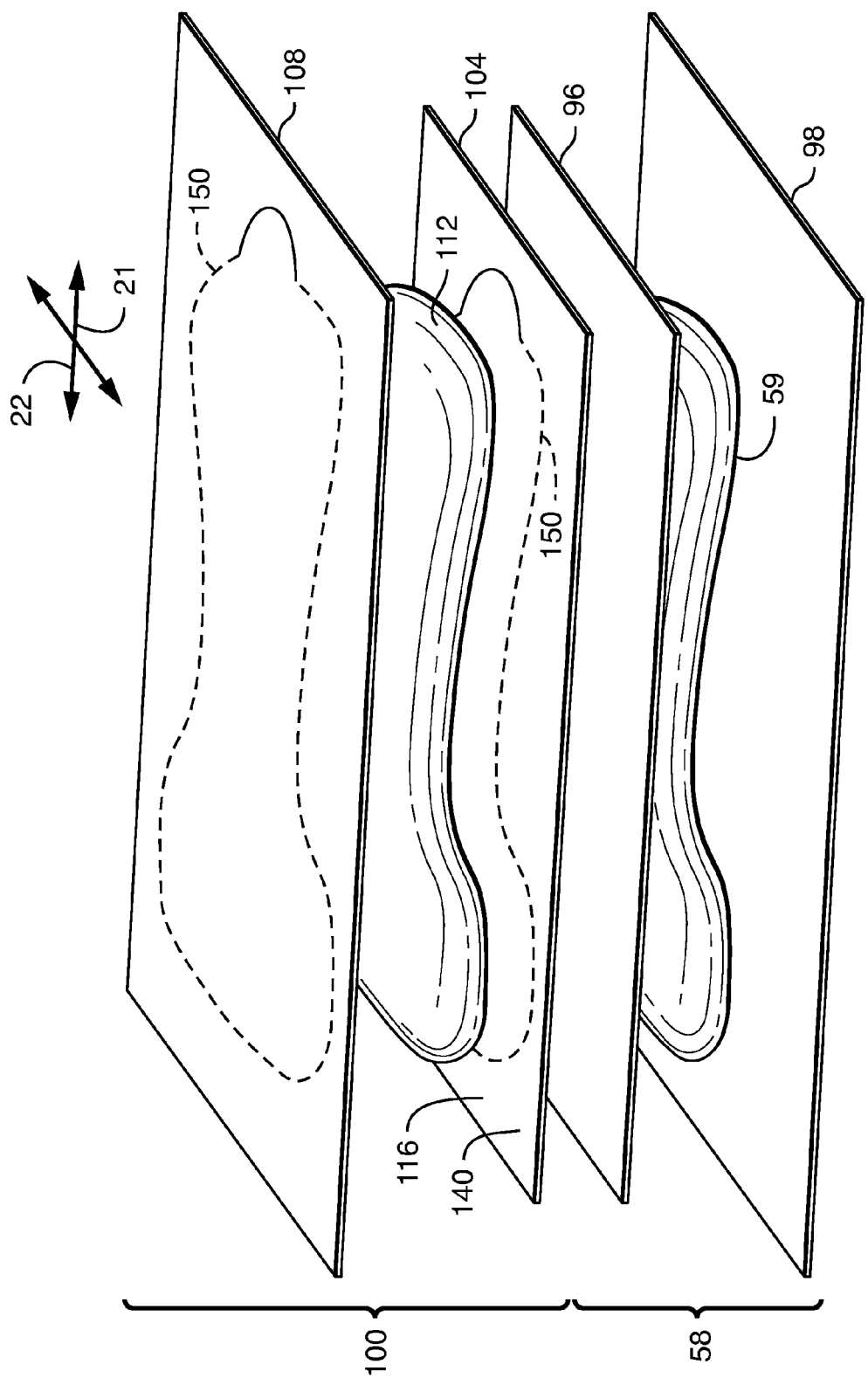
FIG. 6 representatively illustrates an exploded schematic view of the chassis absorbent unit and the absorbent insert of the present disclosure.
Figure 7:
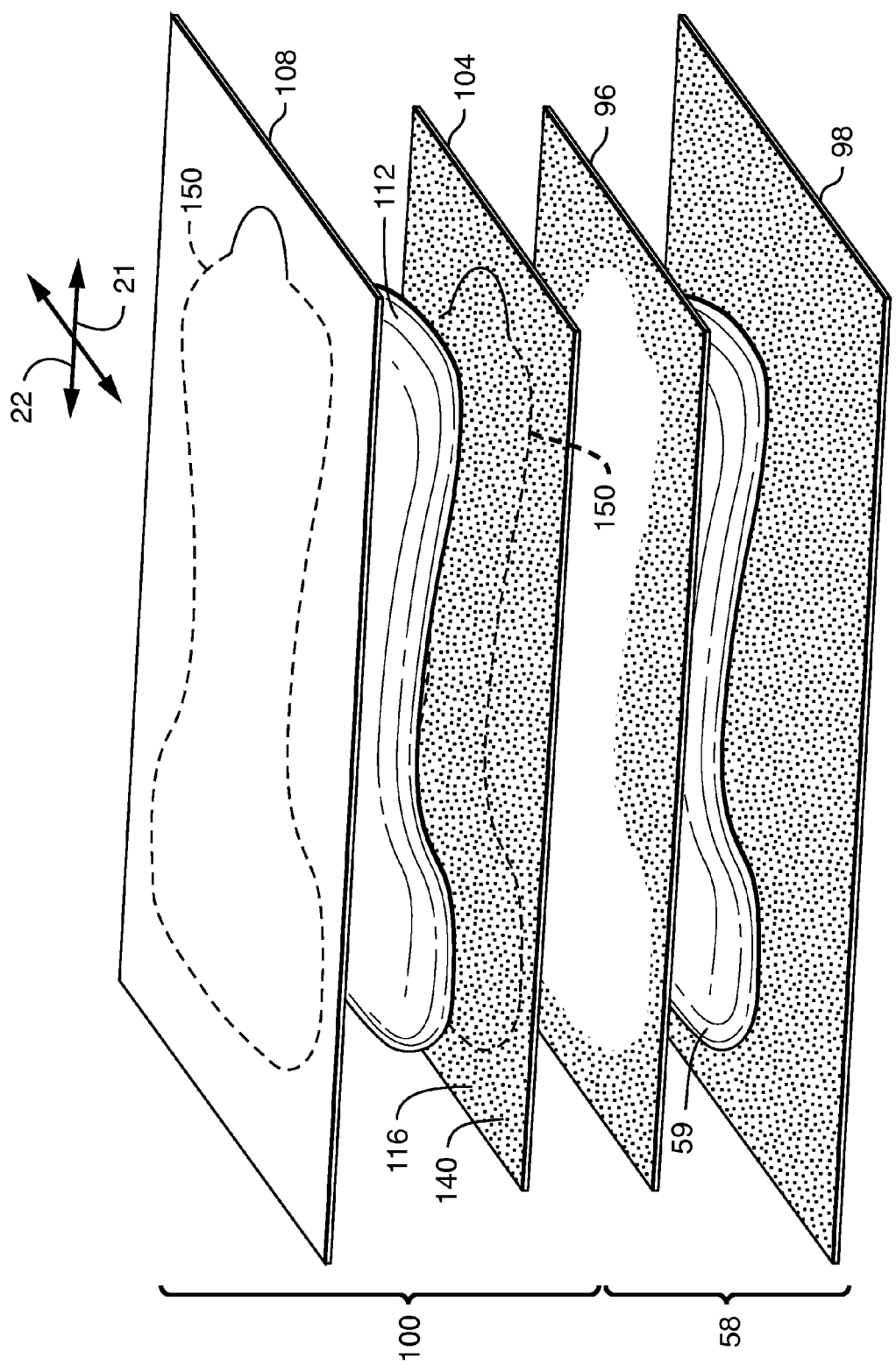
FIG. 7 representatively illustrates an exploded schematic view of the chassis absorbent unit and the absorbent insert of the present disclosure.
Figure 8:
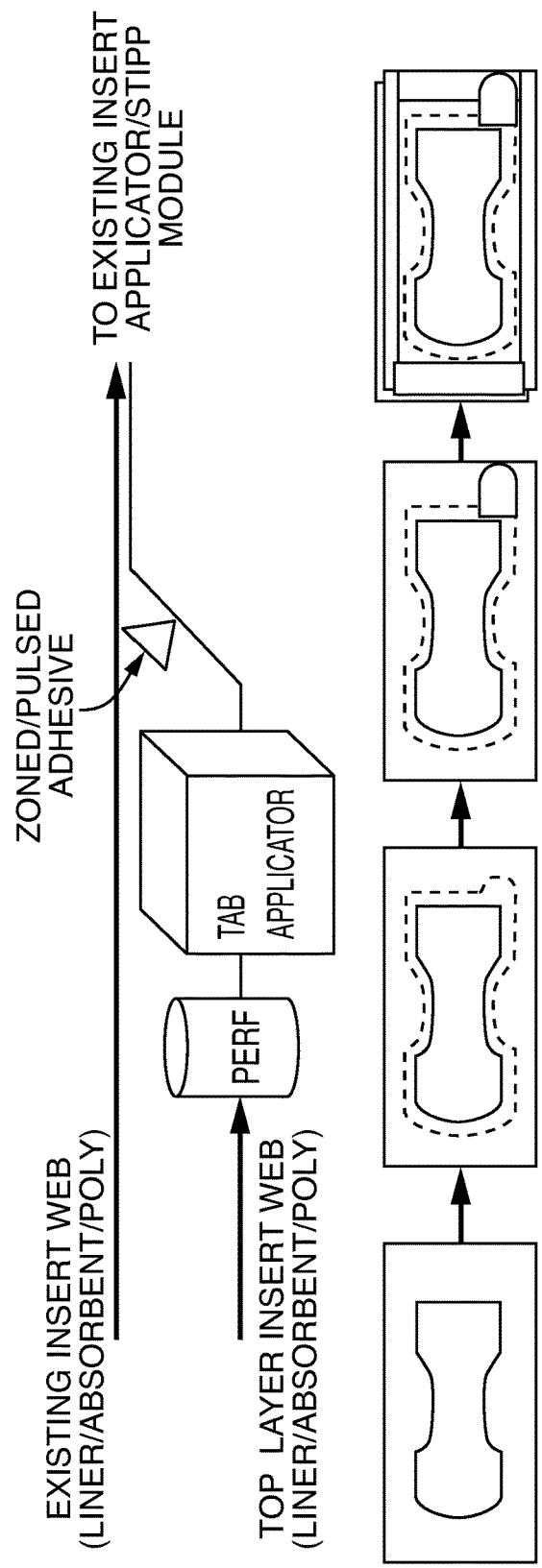
FIGS. 8-16 representatively illustrate schematic plan views of a removal device for the absorbent insert of the present disclosure.

In an alternative aspect illustrated in FIG. 6, the insert topsheet 112 can be full length and width and the chassis topsheet 96 can be full length but narrower. This can provide a more finished look when the removable portion 120 of the absorbent insert 100 is removed. The narrower part can be shaped to match leg cutout and/or crotch elastics. Further, in another aspect illustrated in FIG. 7, the insert topsheet 112 can be full length and the chassis topsheet 96 can be shorter and narrower in a cut and place execution. This can provide a more finished look when the removable portion 120 of the absorbent insert 100 is removed. The chassis topsheet 96 can be shaped to match the contour of the chassis absorbent core shape.

In a cut and place execution, the insert backsheet 104 of the absorbent insert 100 is typically narrower, shorter, and shaped compared to the chassis backsheet 98 or outer cover 24.

The absorbent insert 100 is affixed to the chassis absorbent unit 58 by bonding the absorbent insert 100 to the bonded area 116 of the chassis absorbent unit 58, for example to the chassis topsheet 96, by any suitable method. In one aspect, the absorbent insert 100 is cut and placed on the chassis topsheet 96 and then bonded using ultrasonics. The bonding can occur around the perimeter of the absorbent insert 100, and preferably only adjacent to the perimeter of the absorbent insert 100, and not necessarily along the entire perimeter of the absorbent insert 100. The majority of the absorbent insert 100, particularly away from the perimeter, does not receive bonding. Alternatively, the perimeter bonding can be achieved using adhesive, pressure bonding/embossing, any other suitable method, or any combination of these. In various aspects, the die cutting of the cut and place absorbent insert 100 can follow the contour of chassis absorbent core 59, the insert absorbent core 112, and/or other structure and can include scallops or other decorative shaping.

For an absorbent insert 100 bonded using adhesive, the absorbent insert 100 can be adhesively bonded to the chassis topsheet 96 with zoned adhesive contoured around the insert absorbent core 112. If the absorbent insert 100 includes a tab or other removal device 160 (described below), the tab or other removal device 160 would need to be largely free of adhesive and available for easy access by a user.

The removable portion 120 of the absorbent insert 100 is narrower than the full absorbent insert width. The removable portion 120 is defined by a line of weakness 150 generally following the perimeter of the absorbent insert 100 and/or the perimeter of the insert absorbent core 112, but positioned inwardly from the part of the absorbent insert 100 that is bonded to the chassis absorbent unit 58. As a result, the removable portion 120 can be removed from the absorbent insert 100 and the chassis absorbent unit 58 by separating the removable portion 120 from the absorbent insert 100 at the line of weakness 150 (see, e.g., FIG. 20). The line or lines of weakness 150 need not be continuous on the absorbent insert 100. Some portions of the line of weakness 150 can be replaced with extended cuts or with an edge of the product.

For example, a full-length absorbent insert 100 can have two parallel lines of weakness 150 extending along the length of the absorbent insert 100. Removing the removable portion 120 from the absorbent insert 100 at the line of weakness 150 leaves a resident portion 140 of the absorbent insert 100 attached to the chassis absorbent unit 58. This remaining material can act as a barrier to leakage from the absorbent article 20 or as a means of communicating to the user that one layer has already been removed.

The line of weakness 150 can be accomplished using perforations or any other suitable device for making the absorbent insert 100 preferentially separate at the line of weakness 150 instead of another portion of the absorbent insert 100. For a perforation-based line of weakness 150, the perforations can be repetitive, same-sized and -spaced cuts. The perforations can also have varying lengths and spacings along the line of weakness 150 to aid in removal of a longer removable portion 120. For example, the rear-most part of the absorbent insert 100 can have a perforation pattern with more cut areas compared to the perforation pattern of the forward-most part of the absorbent insert 100, allowing a user to pull back the removable portion 120 to about the middle of the absorbent article 20 then tug it to release the rest of the removable portion 120, rather than needing to peel the removable portion 120 back further than is comfortable or natural. In another example, cut areas can be larger or more frequent in corners and curves to accommodate separating at the line of weakness 150. In various aspects, the density or extent of perforations and cuts can be more limited or more extensive as appropriate to allow for easier removal or more stability in various product types.

In a preferred aspect for a cut-and-place process, the perimeter of the absorbent insert 100 generally follows the shape of the insert absorbent core 112. For a full-length, in-line process, the perimeter of the absorbent insert 100 can parallel the longitudinal axis of the absorbent article 20. In one aspect, the bonded area 116 generally follows the perimeter of the absorbent insert 100, and the line of weakness 150 generally follows the bonded area 116 such that the line of weakness 150 and the bonded area 116 are both generally parallel to the perimeter of the absorbent insert 100 and each other at any given section of the absorbent insert 100. In another aspect, the bonded area 116 generally follows the perimeter of the insert absorbent core 112, and the line of weakness 150 generally follows the bonded area 116 such that the line of weakness 150 and the bonded area 116 are both generally parallel to the perimeter of the insert absorbent core 112 and each other at any given section of the absorbent insert 100. There needs to be appropriate positioning of the bonded area 116 and the line of weakness 150 such that the resident portion 140 of the absorbent insert 100 that is not removable remains bonded to the chassis absorbent unit 58, and that the removable portion 120 maintains structural integrity. To accomplish the latter, the removable portion 120 needs to maintain a sufficient peripheral seal 124 to not break open the insert absorbent core 112 in the removable portion 120 (see, e.g., FIGS. 18 and 19). This peripheral seal 124 can be accomplished during the process of bonding the absorbent insert 100 to the chassis absorbent unit 58 or as a part of manufacturing the absorbent insert 100.

The disposable absorbent article 20 can also be manufactured with more than one absorbent insert 100. The geometries and arrangements of the more than one absorbent inserts 100 can be varied to accommodate the bonding of the more than one absorbent inserts 100, as well as the removal of the removable portions 120 of the more than one absorbent inserts 100. For example, an absorbent insert 100 of relatively smaller dimensions can be bonded to the chassis absorbent unit 58 as described herein, after which a second absorbent insert 102 of relatively larger dimensions can be bonded to the chassis absorbent unit 58 over the top of the first-applied absorbent insert 100. Conversely, an absorbent insert 100 of relatively larger dimensions can be bonded to the chassis absorbent unit 58 as described herein, after which a second absorbent insert 102 of relatively smaller dimensions can be bonded to the insert topsheet of the first-applied absorbent insert 100. Any other suitable arrangement of multiple absorbent inserts 100, 102 can be employed as well.

In various aspects illustrated in FIGS. 8-16, the absorbent insert 100 is provided with a tab or other removal device 160 to assist the user in removing the removable portion 120 from the absorbent insert 100. In one aspect, an extended cut 162 that is finger sized and adjacent one (see FIG. 8) or both (see FIG. 9) ends of the removable portion 120 allows a user to insert a finger under the removable portion 120 to initiate the removal of the removable portion 120. In another aspect illustrated in FIG. 10, the absorbent insert 100 can include a tab 168 that extends from the removable portion 120 beyond the line of weakness 150. The tab 168 can be made from one or both of the insert topsheet 109 and insert backsheet 104, and provides the user with a graspable device to initiate the removal of the removable portion 120.

Figure 11:
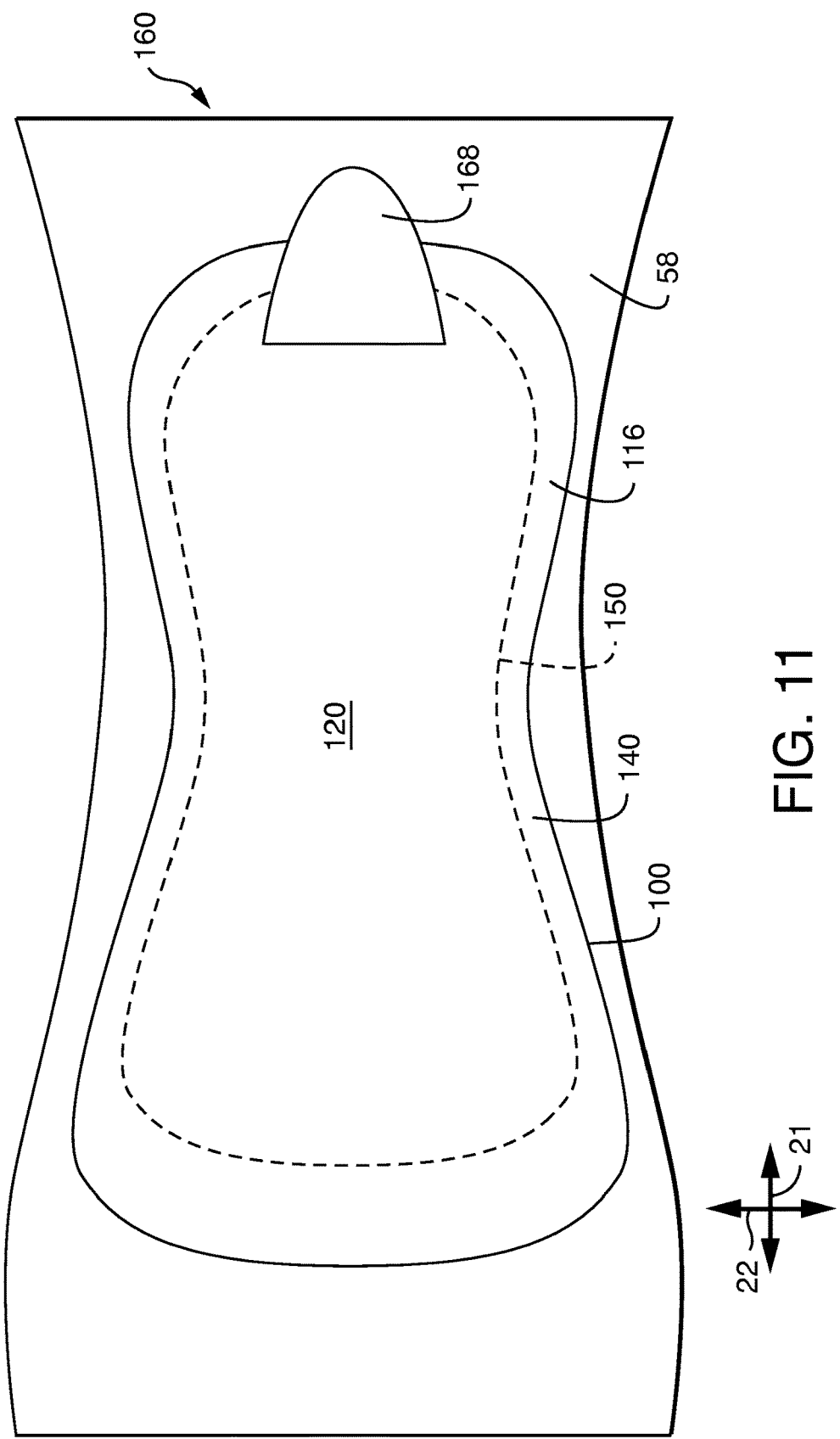
Figure 12:
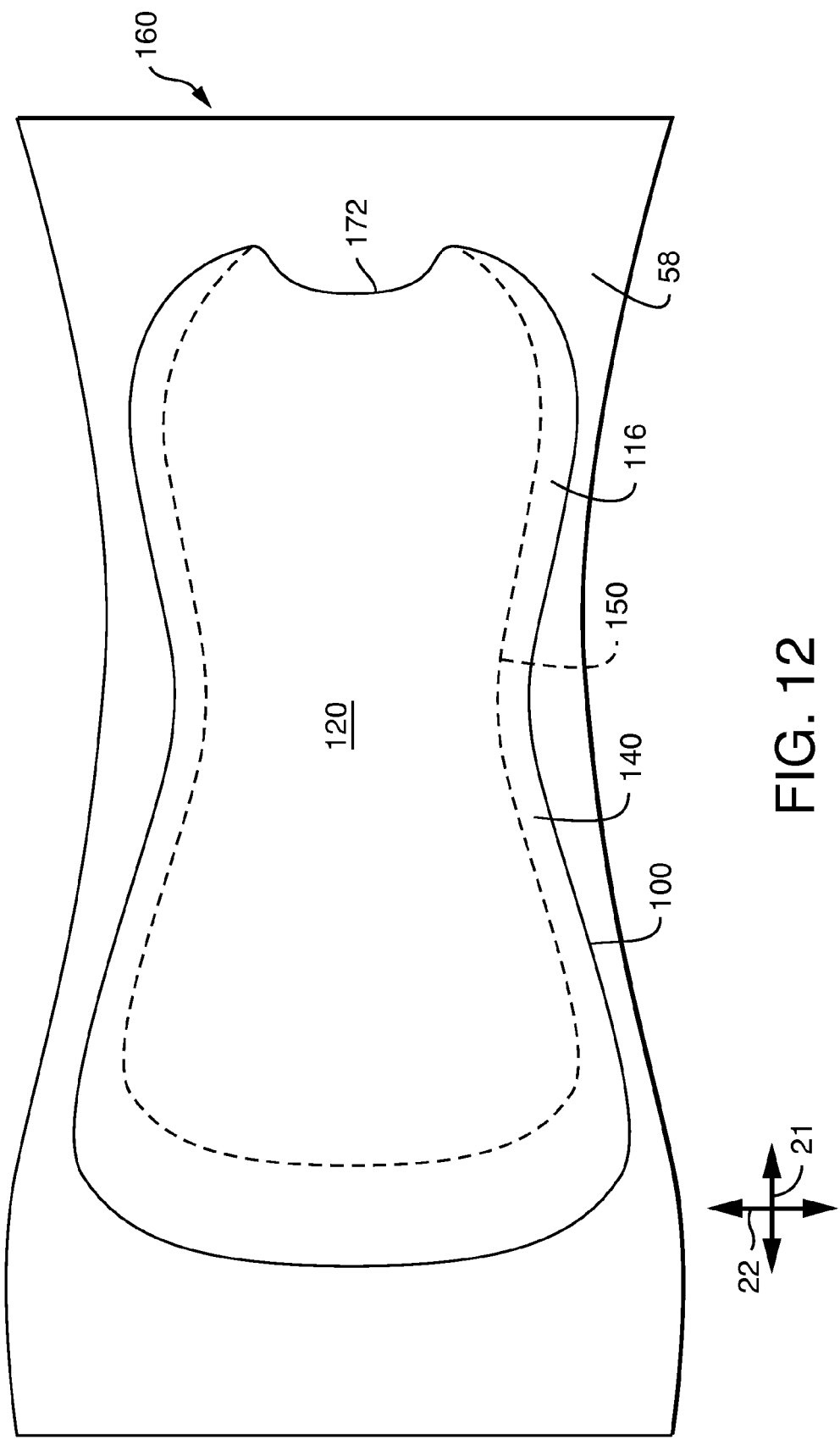

In still another aspect illustrated in FIG. 11, a tab 168 can be attached to the removable portion 120 as a separate piece of material, where the bond between the tab 168 and the removable portion 120 needs to be strong enough to enable the user to initiate the removal of the removable portion 120 without tearing the tab 168 from the removable portion 120. In yet another aspect illustrated in FIG. 12, there can be an unbonded notch 172 in the absorbent insert 100 that allows a user to insert a finger under the removable portion 120 to initiate the removal of the removable portion 120.

Figure 13:
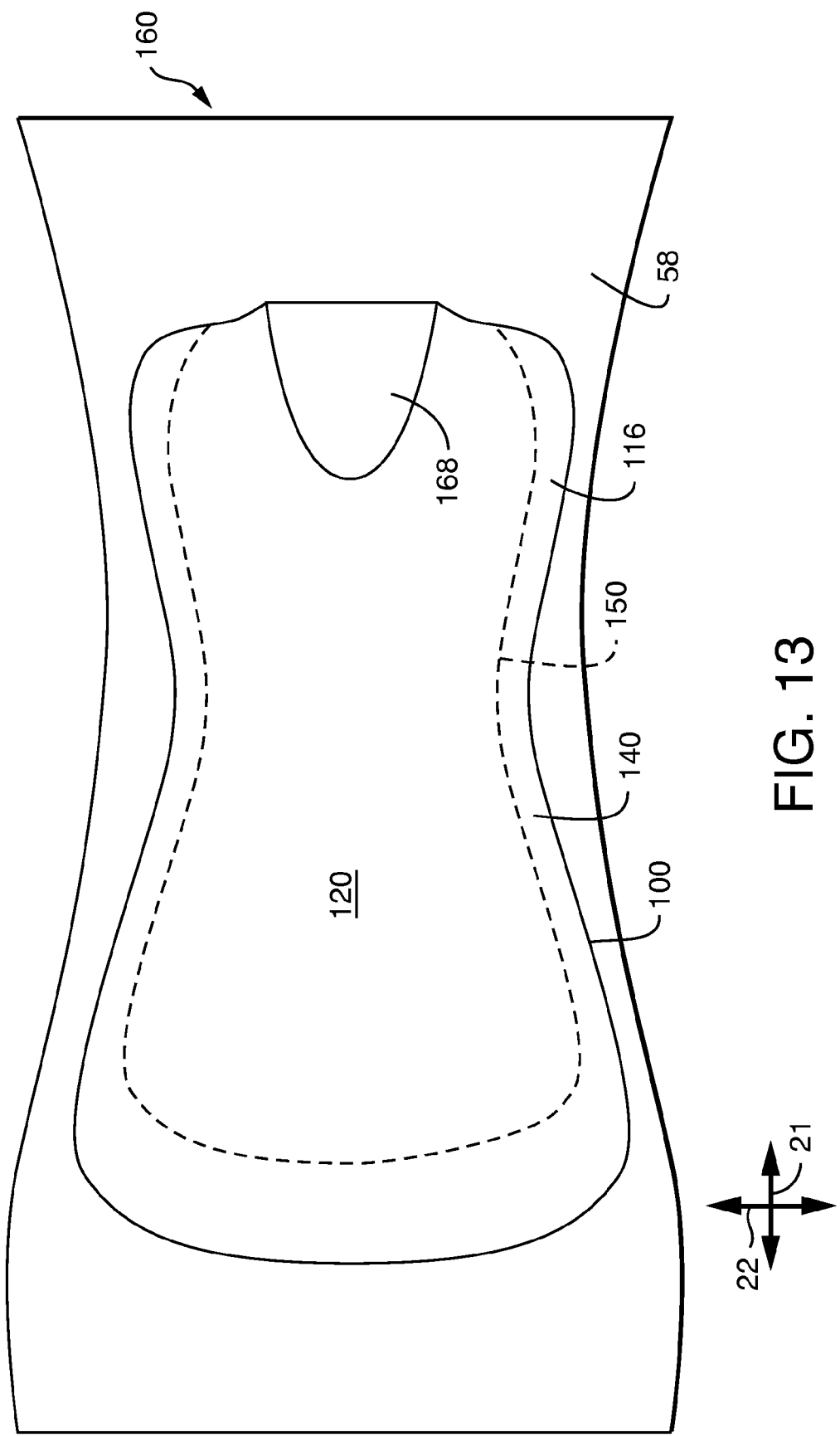
Figure 14:
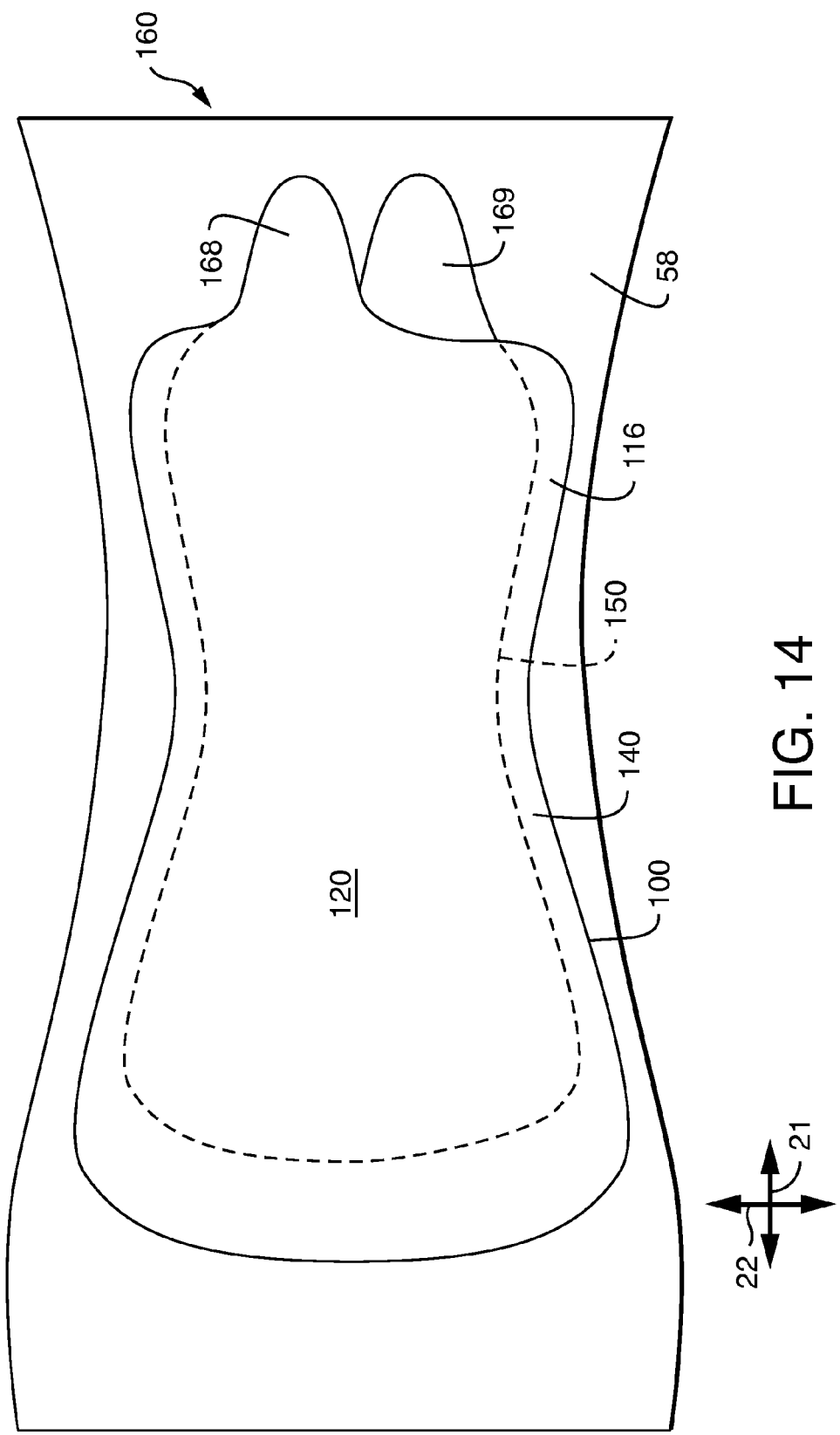
Figure 15:
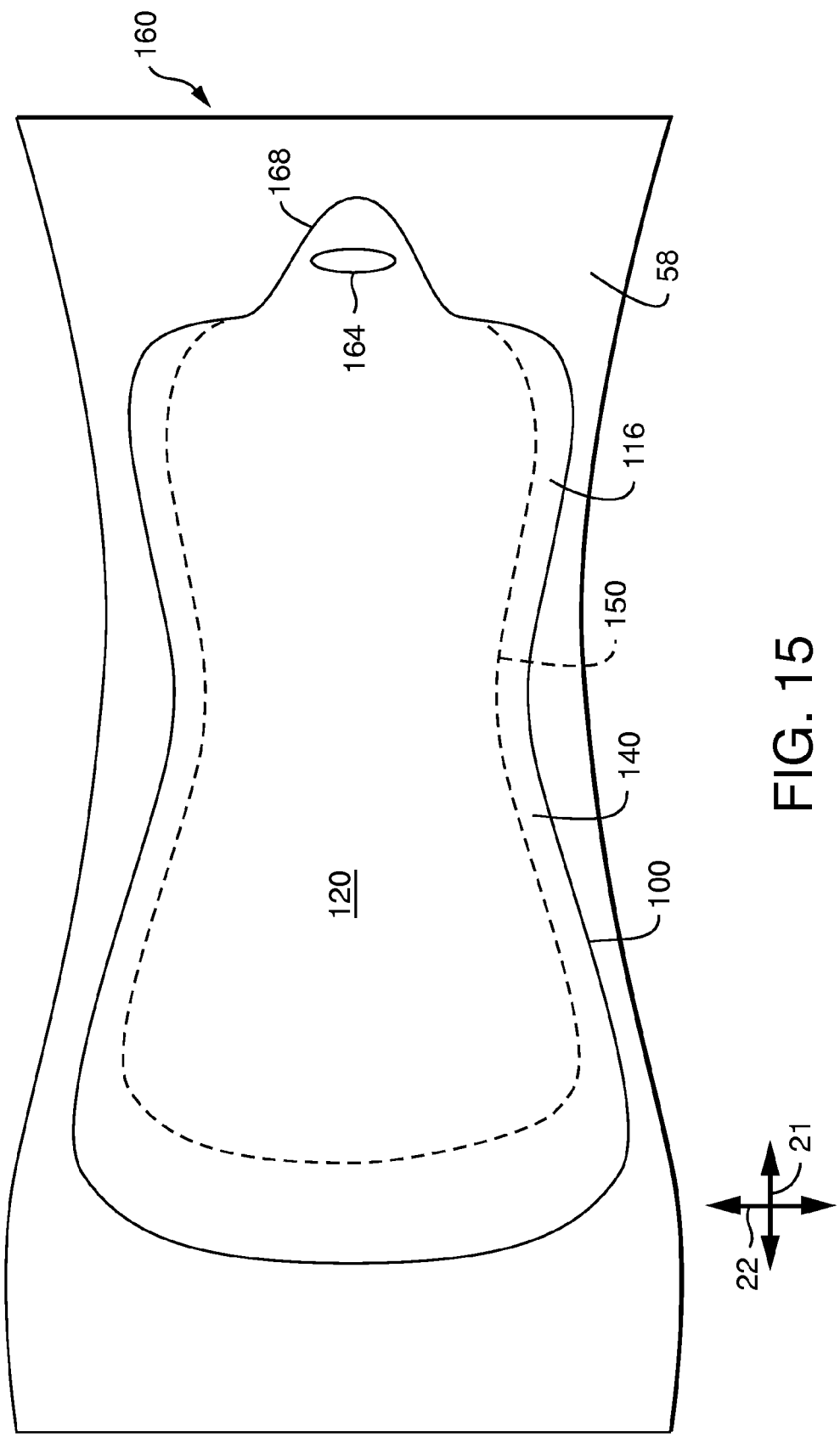

In an alternative aspect illustrated in FIG. 13, a tab 168 either added to the removable portion 120 or a part of the removable portion 120 can be folded over the removable portion 120 and removably attached such that a user can peel up the tab 168 and have a graspable device to initiate the removal of the removable portion 120. In another alternative aspect illustrated in FIG. 14, the absorbent insert 100 can have multiple removable portions with tabs 168, 169 that can be staggered in shape and/or position. For example, the tab 168 on top can be smaller, and the tab 169 on the bottom can be larger. Alternatively, any tab 168 described herein or the absorbent insert 100 can have an aperture, hole, slot, or other access point 164 for easier grasping, as illustrated in FIG. 15.

Figure 9:
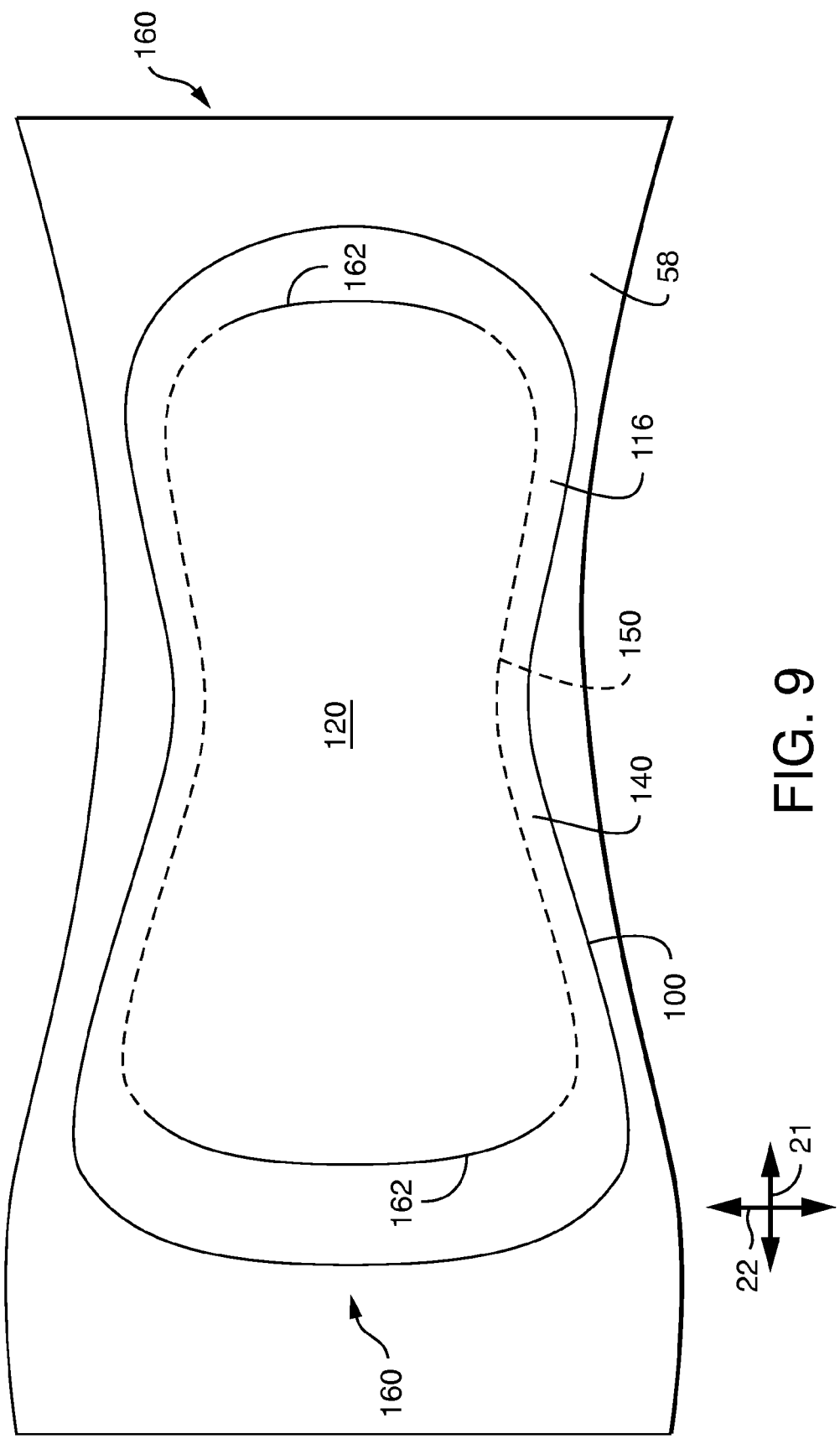
Figure 10:
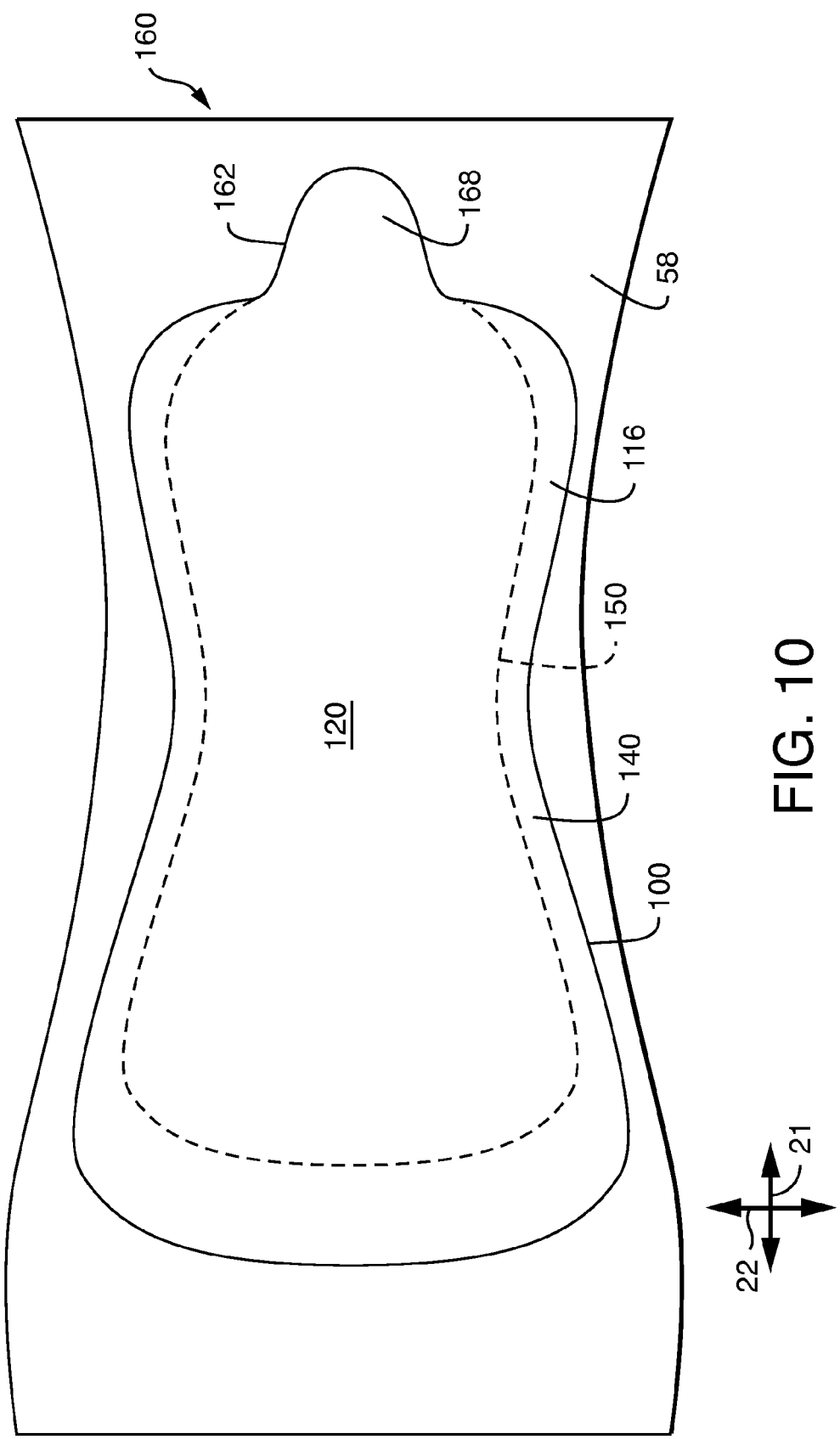
Figure 16:
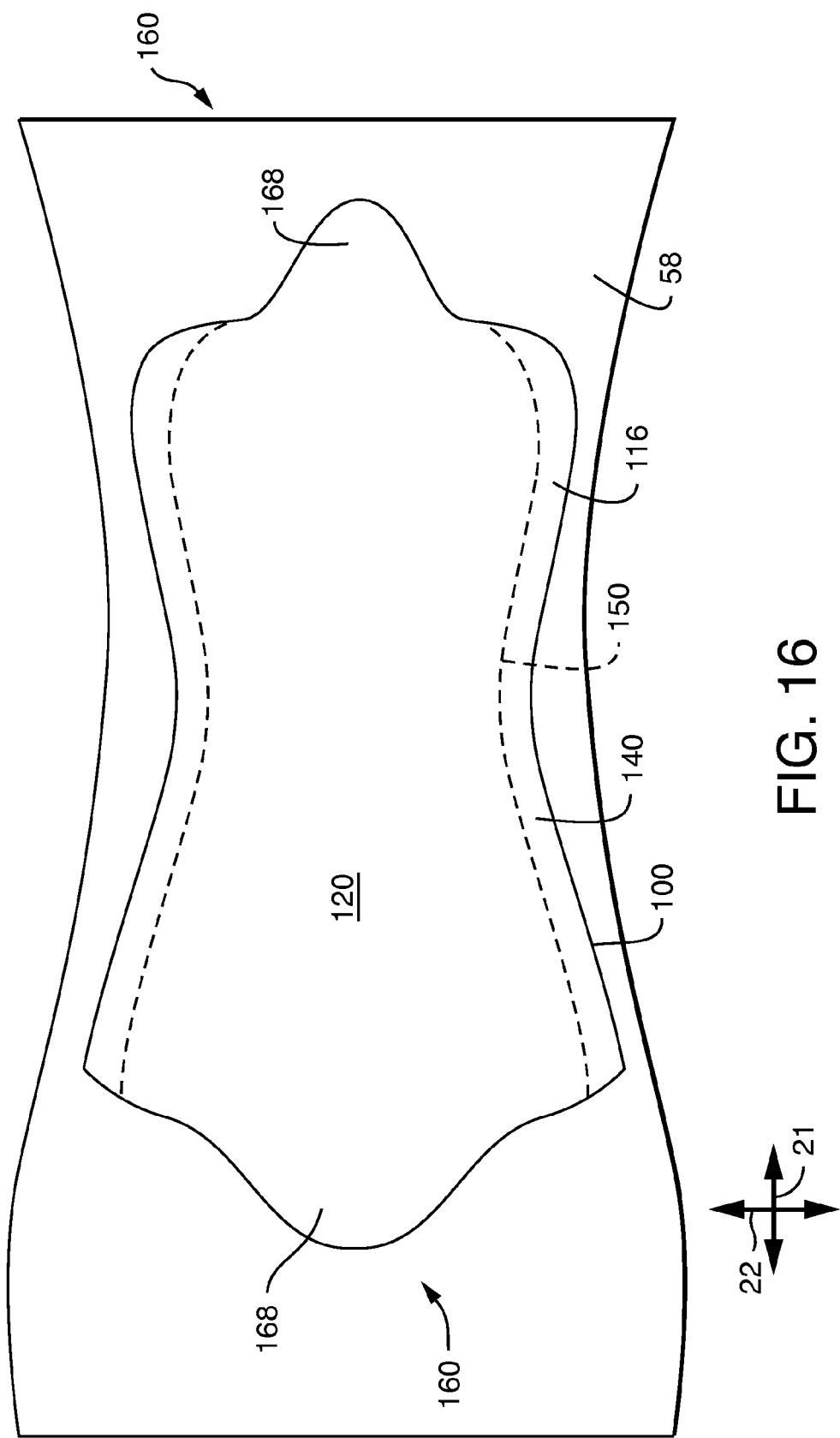

In other aspects illustrated in FIG. 16, the tabs 168 can be disposed on one or both ends of the removable portion 120 can be configured to help confine the removable portion 120 for disposal. In still other aspects (not shown), a small strip of hook material (or light adhesive, or cohesive material) can be positioned on the insert backsheet 104 of the removable portion 120 to help confine the removable portion 120 for disposal, to keep the absorbent insert 100 from shifting during use, or for both reasons. In the aspect of FIG. 9, one or both ends of the removable portion 120 can be free of bonding (not shown) instead of an extended cut 162 to allow a user to grasp the removable portion 120. Similarly, in the aspect of FIG. 16, one or both ends of the removable portion 120 can be free of bonding (not shown), with or without a tab 168, to allow a user to grasp the removable portion 120.

Figure 17:
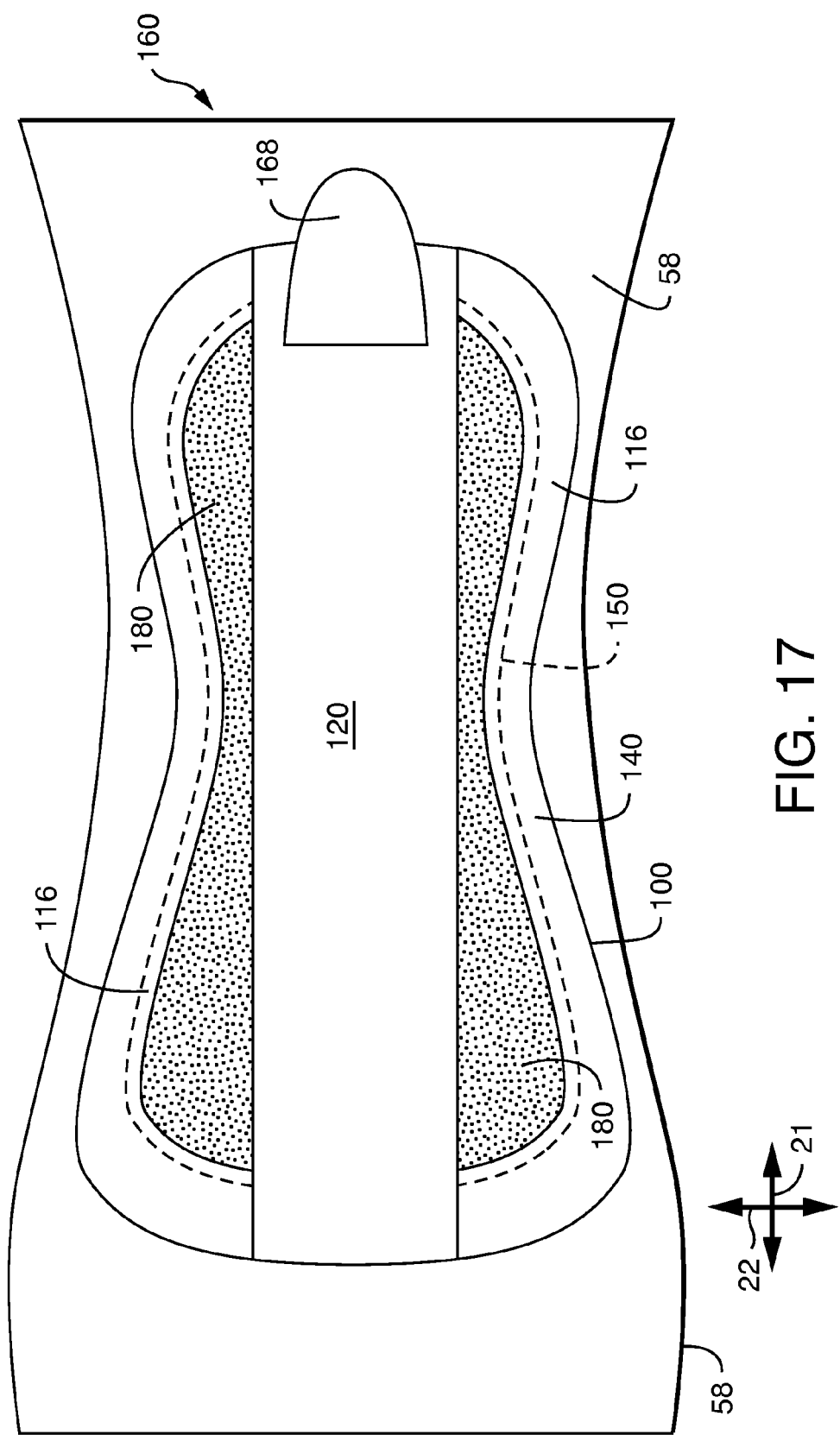
FIG. 17 representatively illustrates a schematic plan view of flaps on an absorbent insert of the present disclosure.
Figure 18:
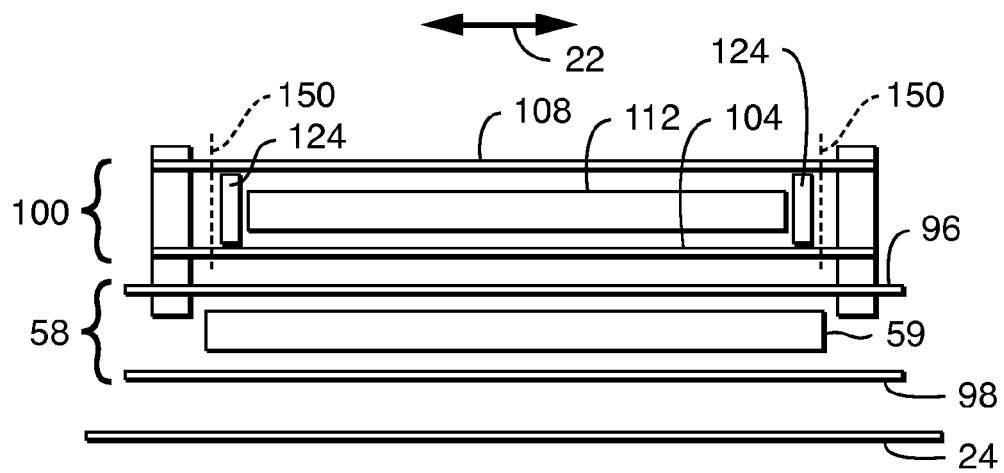
FIG. 18 representatively illustrates a schematic elevation cross section taken at the crotch region of the disposable absorbent article of the present disclosure, with the absorbent insert in place.
Figure 19:
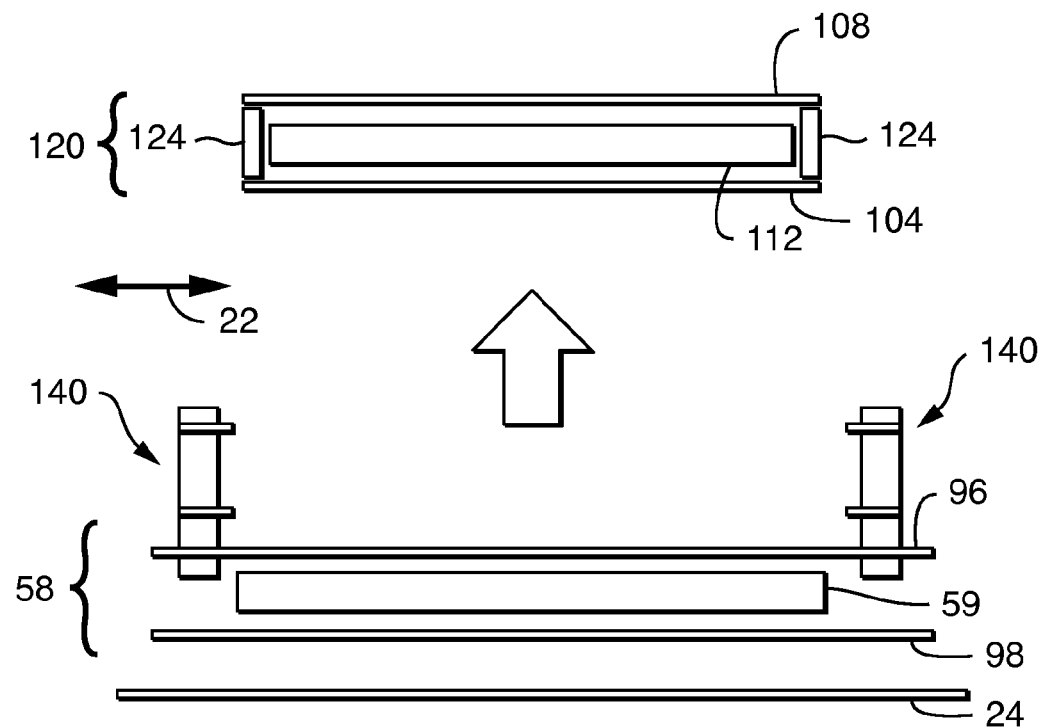
FIG. 19 representatively illustrates a schematic elevation cross section taken at the crotch region of the disposable absorbent article of the present disclosure, with the removable portion of the absorbent insert separated from the absorbent insert at the line of weakness, leaving the resident portion attached to the chassis absorbent unit.
Figure 20:
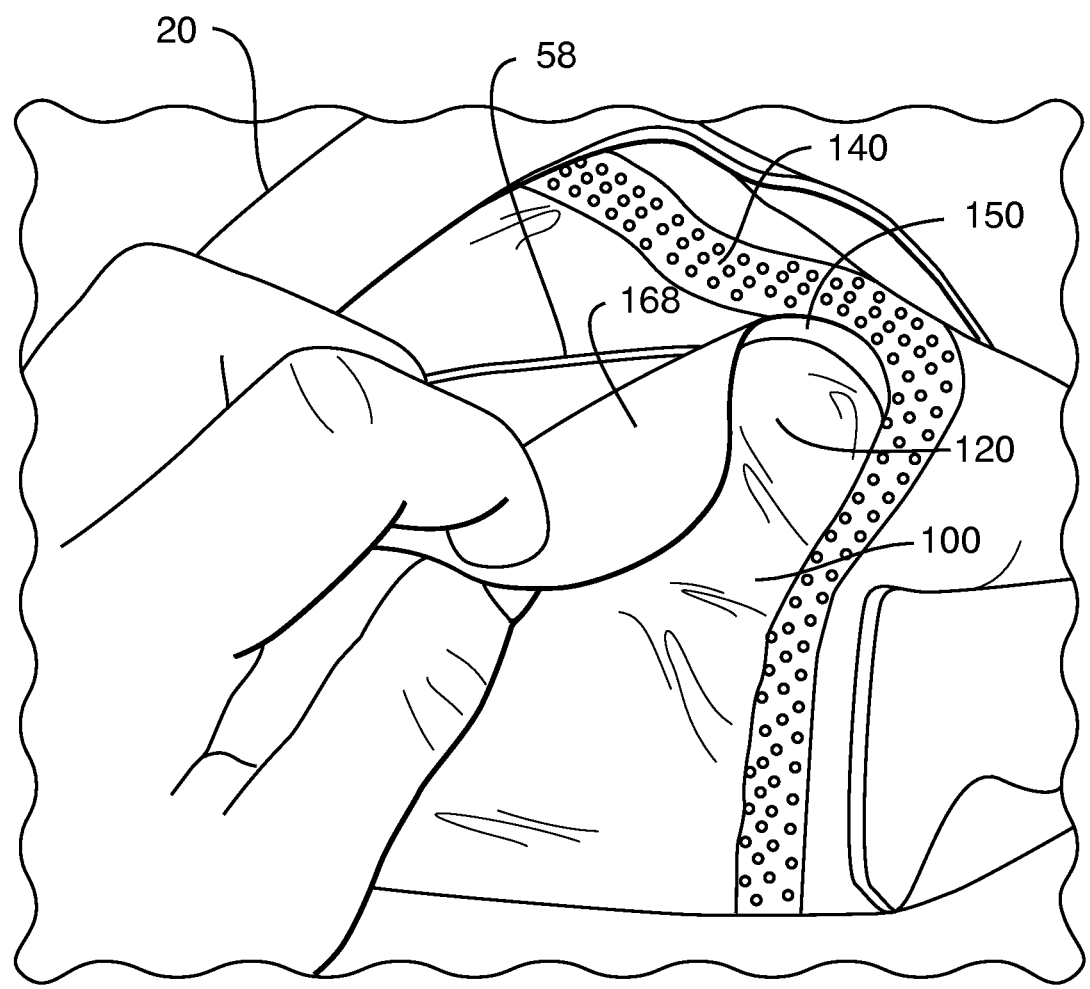
FIG. 20 representatively illustrates in partial schematic perspective the partial removal of the removable portion of an absorbent insert from the absorbent insert at the line of weakness, leaving the resident portion attached to the chassis absorbent unit.

The absorbent article 20 can also include flaps 180 on the absorbent insert 100, as illustrated in FIG. 17. For flaps 180 provided on the absorbent insert 100, the flaps 180 can be applied in a linear profile and bonded with a shaped tack line extending to the edge of the absorbent insert 100 and inwardly from the line of weakness 150. Sealing the flaps 180 inwardly of the line of weakness 150 allows the flaps 180 to prevent urine leakage both from the absorbent article 20 and through the line of weakness 150 to the other portions of the absorbent article 20. The flaps 180 are largely disposed inwardly of the line of weakness 150. The line of weakness 150 extends across the flap 180, insert topsheet 108, and insert backsheet 104 of the removable portion 120. In this aspect, the flaps 180 run longitudinally along the length of the absorbent insert 100 and extend beyond the line of weakness 150. The flaps 180 are tacked down in the bonded area 116 adjacent the perimeter of the absorbent insert 100. The absorbent insert 100 itself is sealed inwardly (approximately 10 mm) of the line of weakness 150, which maintains the structural integrity of the removable portion 120, and keeps urine in the product from reaching the line of weakness 150. The area of the chassis absorbent unit 58 below the removable portion 120 can also include flaps in a suitable manner, either inwardly or outwardly from the line of weakness 150.

In use, a user places a disposable absorbent article 20 of the present disclosure on the user, where the disposable absorbent article includes an absorbent insert 100. After the user insults the disposable absorbent article 20, the user employs the removal device 160 or by any other means causes the removable portion 120 to be separated from the absorbent insert 100 at the line of weakness 150. Because of the arrangement described herein, this operation can be accomplished without removing the user's clothing and usually without removing the disposable absorbent article 20. The removable portion 120 is discarded, and the user is left with a fresh chassis absorbent unit 58 and a resident portion 140 to contain future insults.

In a first particular aspect, a multiple use absorbent article includes a chassis absorbent unit having a chassis topsheet, a chassis backsheet, and a chassis absorbent core sandwiched between the chassis topsheet and the chassis backsheet; and an absorbent insert bonded to the chassis absorbent unit, a removable portion of the absorbent insert configured to be selectively removable from the chassis absorbent unit, wherein the absorbent insert comprises an insert topsheet, an insert backsheet, and an insert absorbent core sandwiched between the insert topsheet and the insert backsheet, the absorbent insert further including a line of weakness that provides for separation of the absorbent insert into a removable portion configured to be removed from the chassis absorbent unit, and a resident portion that remains bonded to the chassis absorbent unit.

A second particular aspect includes the first particular aspect, wherein one or both of the insert topsheet and the insert backsheet are bonded to one or both of the chassis topsheet and the chassis backsheet.

A third particular aspect includes the first and/or second aspect, wherein the insert backsheet is bonded to the chassis topsheet.

A fourth particular aspect includes one or more of aspects 1-3, wherein the insert topsheet and the insert backsheet are bonded to the chassis topsheet.

A fifth particular aspect includes one or more of aspects 1-4, wherein the insert backsheet is of a dimension that extends beyond the dimension of the insert topsheet.

A sixth particular aspect includes one or more of aspects 1-5, wherein the insert topsheet is of a dimension that extends beyond the dimension of the insert backsheet.

A seventh particular aspect includes one or more of aspects 1-6, wherein the line of weakness includes perforations.

An eighth particular aspect includes one or more of aspects 1-7, wherein the absorbent insert is ultrasonically bonded to the chassis absorbent unit.

A ninth particular aspect includes one or more of aspects 1-8, wherein the absorbent insert is adhesively bonded to the chassis absorbent unit.

A tenth particular aspect includes one or more of aspects 1-9, wherein the absorbent article is a garment-like absorbent article.

An eleventh particular aspect includes one or more of aspects 1-10, wherein the absorbent article is a pad-like absorbent article.

A twelfth particular aspect includes one or more of aspects 1-11, wherein the line of weakness is disposed in one or both of the insert topsheet and the insert backsheet.

A thirteenth particular aspect includes one or more of aspects 1-12, further including flaps disposed on the absorbent insert.

A fourteenth particular aspect includes one or more of aspects 1-13, wherein the line of weakness extends across the flaps.

A fifteenth particular aspect includes one or more of aspects 1-14, further including a second absorbent insert having a second insert topsheet, a second insert backsheet, and a second insert absorbent core, the second insert absorbent core having a core peripheral outer edge and being sandwiched between the second insert topsheet and the second insert backsheet, the second absorbent insert including a peripheral sealing region sealing the second insert topsheet to the second insert backsheet outside the core peripheral outer edge, the second absorbent insert including a separable line of weakness within or adjacent to the peripheral sealing region of the second absorbent insert, wherein the second insert backsheet is bonded to one or both of the first insert topsheet and the chassis topsheet.

A sixteenth particular aspect includes one or more of aspects 1-15, wherein the insert topsheet is narrower than the chassis topsheet.

A seventeenth particular aspect includes one or more of aspects 1-16, wherein the chassis topsheet is narrower than the insert topsheet.

In an eighteenth particular aspect, a multiple use absorbent article includes a chassis absorbent unit having a liquid permeable chassis topsheet, a liquid impermeable chassis backsheet, and a chassis absorbent core sandwiched between the chassis topsheet and the chassis backsheet; and an absorbent insert bonded to the chassis absorbent unit, a removable portion of the absorbent insert configured to be selectively removable from the chassis absorbent unit, wherein the absorbent insert comprises an insert topsheet, an insert backsheet, and an insert absorbent core sandwiched between the insert topsheet and the insert backsheet, the insert absorbent core sealed by a peripheral sealing region between the insert topsheet and the insert backsheet adjacent at least a peripheral edge of the insert topsheet and the insert backsheet; the absorbent insert further including a line of weakness disposed within the peripheral sealing region that provides for separation of the absorbent insert into a removable portion configured to be removed from the chassis absorbent unit, and a resident portion that remains bonded to the chassis absorbent unit.

A nineteenth particular aspect includes the eighteenth particular aspect, wherein the line of weakness extends through the insert topsheet and the insert backsheet.

A twentieth particular aspect includes the eighteenth and/or nineteenth aspect, wherein the resident portion includes material from one or both of the insert topsheet and the insert backsheet.

Other objects and advantages of the present disclosure will become more apparent to those skilled in the art in view of the following description and the accompanying drawings.

The disclosure has been described with reference to various specific and illustrative aspects and techniques. However, it should be understood that many variations and modifications can be made while remaining within the spirit and scope of the disclosure. Many alternatives, modifications and variations will be apparent to those skilled in the art in light of the foregoing description. Accordingly, this disclosure is intended to embrace all such alternatives, modifications, and variations that fall within the spirit and scope of the appended claims.

We claim:

1. A multiple use absorbent article comprising:
   a chassis absorbent unit having a chassis topsheet, a chassis backsheet, and a chassis absorbent core sandwiched between the chassis topsheet and the chassis backsheet; and
   an absorbent insert bonded to the chassis absorbent unit, a removable portion of the absorbent insert configured to be selectively removable from the chassis absorbent unit, wherein the absorbent insert comprises an insert topsheet, an insert backsheet bonded to the chassis topsheet, flaps positioned inwardly of a pair of longitudinal direction side edges of the absorbent insert, and an insert absorbent core sandwiched between the insert topsheet and the insert backsheet, the absorbent insert further including a line of weakness that provides for separation of the absorbent insert into the removable portion configured to be removed from the chassis absorbent unit, and a resident portion that remains bonded to the chassis absorbent unit, wherein the line of weakness extends across the flaps.

2. The multiple use absorbent article of claim 1, wherein the insert backsheet is of a dimension that extends beyond the dimension of the insert topsheet.

3. The multiple use absorbent article of claim 1, wherein the insert topsheet is of a dimension that extends beyond the dimension of the insert backsheet.

4. The multiple use absorbent article of claim 1, wherein the line of weakness includes perforations.

5. The multiple use absorbent article of claim 1, wherein the absorbent insert is ultrasonically bonded to the chassis absorbent unit.

6. The multiple use absorbent article of claim 1, wherein the absorbent insert is adhesively bonded to the chassis absorbent unit.

7. The multiple use absorbent article of claim 1, wherein the absorbent article is a garment-like absorbent article.

8. The multiple use absorbent article of claim 1, wherein the absorbent article is a pad-like absorbent article.

9. The multiple use absorbent article of claim 1, wherein the line of weakness is disposed in one or both of the insert topsheet and the insert backsheet.

10. The multiple use absorbent article of claim 1, further comprising a second absorbent insert having a second insert topsheet, a second insert backsheet, and a second insert absorbent core, the second insert absorbent core having a core peripheral outer edge and being sandwiched between the second insert topsheet and the second insert backsheet, the second absorbent insert including a peripheral sealing region sealing the second insert topsheet to the second insert backsheet outside the core peripheral outer edge, the second absorbent insert including a separable line of weakness within or adjacent to the peripheral sealing region of the second absorbent insert, wherein the second insert backsheet is bonded to one or both of the first insert topsheet and the chassis topsheet.

11. The multiple use absorbent article of claim 1, wherein the insert topsheet is narrower than the chassis topsheet.

12. The multiple use absorbent article of claim 1, wherein the chassis topsheet is narrower than the insert topsheet.

13. A multiple use absorbent article comprising:
   a chassis absorbent unit having a liquid permeable chassis topsheet, a liquid impermeable chassis backsheet, and a chassis absorbent core sandwiched between the chassis topsheet and the chassis backsheet; and
   an absorbent insert bonded to the chassis absorbent unit, a removable portion of the absorbent insert configured to be selectively removable from the chassis absorbent unit, wherein the absorbent insert comprises an insert topsheet, an insert backsheet bonded to the chassis topsheet, flaps positioned inwardly of a pair of longitudinal direction side edges of the absorbent insert, and an insert absorbent core sandwiched between the insert topsheet and the insert backsheet, the insert absorbent core sealed by a peripheral sealing region between the insert topsheet and the insert backsheet adjacent at least a peripheral edge of the insert topsheet and the insert backsheet;
   the absorbent insert further including a line of weakness disposed within the peripheral sealing region that provides for separation of the absorbent insert into the removable portion configured to be removed from the chassis absorbent unit, and a resident portion that remains bonded to the chassis absorbent unit, wherein the line of weakness extends across the flaps.

14. The multiple use absorbent article of claim 13, wherein the line of weakness extends through the insert topsheet and the insert backsheet.

15. The multiple use absorbent article of claim 13, wherein the resident portion includes material from one or both of the insert topsheet and the insert backsheet.

* * * * *